(12) United States Patent
Anderson

(10) Patent No.: US 11,515,045 B1
(45) Date of Patent: Nov. 29, 2022

(54) PREDICTING RISK OF RUNNING-RELATED INJURY USING A MACHINE LEARNING MODEL AND RELATED MACHINE LEARNING TRAINING METHODS

(71) Applicant: Bjorn Gunnar Anderson, Jacksonville Beach, FL (US)

(72) Inventor: Bjorn Gunnar Anderson, Jacksonville Beach, FL (US)

( * ) Notice: Subject to any disclaimer, the term of this patent is extended or adjusted under 35 U.S.C. 154(b) by 0 days.

(21) Appl. No.: 17/714,963

(22) Filed: Apr. 6, 2022

Related U.S. Application Data

(60) Provisional application No. 63/174,506, filed on Apr. 13, 2021.

(51) Int. Cl.
  *G16H 50/30* (2018.01)
  *G16H 20/30* (2018.01)
  *G16H 50/20* (2018.01)

(52) U.S. Cl.
  CPC ............ *G16H 50/30* (2018.01); *G16H 20/30* (2018.01); *G16H 50/20* (2018.01)

(58) Field of Classification Search
  CPC ......... G16H 50/30; G16H 20/30; G16H 50/20
  USPC .......................................................... 705/2
  See application file for complete search history.

(56) References Cited

U.S. PATENT DOCUMENTS

| | | | |
|---|---|---|---|
| 2003/0181832 A1* | 9/2003 | Carnahan | A61B 5/4528 600/595 |
| 2017/0188894 A1* | 7/2017 | Chang | A61B 5/1121 |
| 2018/0264318 A1* | 9/2018 | Fung | A63B 22/0285 |
| 2019/0282131 A1* | 9/2019 | Chang | A61B 5/1121 |
| 2020/0000414 A1 | 1/2020 | McCord et al. | |
| 2020/0108291 A1 | 4/2020 | Piazza et al. | |
| 2022/0261990 A1* | 8/2022 | Goldberg | G06N 20/00 |
| 2022/0293272 A1* | 9/2022 | Pang | G16H 10/20 |

OTHER PUBLICATIONS

Kakavas, G. et al., Artificial intelligence. A tool for sports trauma prediction, Injury (2019), https://doi.org/10.1016/j.injury.2019.08.033.

Ramskov D, et al., Run Clever—No difference in risk of injury when comparing progression in running volume and running intensity in recreational runners: A randomised trial, BMJ Open Sport Exerc Med 2018;4:e000333. doi:10.1136/bmjsem-2017-000333.

(Continued)

*Primary Examiner* — Michael Tomaszewski
*Assistant Examiner* — Rachael Sojin Stone

(57) ABSTRACT

Machine learning-based systems and methods for predicting running-related injuries and related training methods are described herein. An example method for training a machine learning model includes receiving a dataset including running-related data, where the running-related data includes a plurality of samples tagged with respective running-related injury labels. The method also includes augmenting the dataset, where the augmented dataset further includes a plurality of synthetic samples tagged with respective running-related injury labels. The method further includes training a machine learning model using the augmented dataset. The trained machine learning model is configured for predicting risk of running-related injury.

29 Claims, 22 Drawing Sheets

(56) References Cited

OTHER PUBLICATIONS

Nielsen, R. O. et al., Classifying Running Related Injuries Based Upon Etiology, With Emphasis on Volume and Pace, The International Journal of Sports Physical Therapy, vol. 8, No. 2, Apr. 2013, pp. 172-179.

Dijkhuis, T. et al., Prediction of Running Injuries from Training Load: a Machine Learning Approach, eTELEMED 2017 : The Ninth International Conference on eHealth, Telemedicine, and Social Medicine, 2017, pp. 109-110.

Hutchinson, A., The Elusive Art of Predicting Running Injuries, Online.com, May 7, 2021, https://www.outsideonline.com/2423442/running-injuries-prediction-research (accessed May 8, 2021).

* cited by examiner

FIG. 2A

*Garmin Activities Download - Grouped By Week*

| Time Period | Activities | Total Distance | Max Distance | Total Activity Time | Injury Label |
|---|---|---|---|---|---|
| 09/28/2020 | 7 | 46.83 mi | 9.23 mi | 6:13:55 h:m:s | 0 |
| 09/21/2020 | 6 | 41.93 mi | 9.02 mi | 5:47:04 h:m:s | 0 |
| 09/14/2020 | 6 | 40.62 mi | 7.65 mi | 5:22:30 h:m:s | 0 |
| 09/07/2020 | 7 | 8.80 mi | 4.07 mi | 1:14:10 h:m:s | 0 |
| 08/31/2020 | 6 | 41.78 mi | 8.45 mi | 5:34:14 h:m:s | 1 |
| 08/24/2020 | 8 | 49.86 mi | 11.43 mi | 6:39:54 h:m:s | 0 |
| 08/17/2020 | 8 | 46.07 mi | 11.32 mi | 6:11:43 h:m:s | 0 |
| 08/10/2020 | 10 | 50.06 mi | 11.06 mi | 0:33:42 h:m:s | 0 |
| 08/03/2020 | 8 | 47.43 mi | 9.83 mi | 6:15:06 h:m:s | 0 |

*FIG. 2B*

| Date | Distance 9T | Distance 8T | Distance 7T | Time 9T | Time 8T | Time 7T | Intensity 8T | Intensity 7T |
|---|---|---|---|---|---|---|---|---|
| 12/13/2020 8:23 | 47.07 | 48.2 | 46.8 | 6h 4m | 8h 16m 52s 33ms | 0h 9m 42s 408ms | 7m 43s 990ms | 0h 7m 49s 128ms | 0h 7m 50s 764ms |
| 12/6/2020 7:35 | 49.57 | 47.4 | 46.3 | 6h 30m 6s | 8h 8m 21s 33ms | 0h 6m 14s 025ms | 7m 55s 652ms | 0h 7m 46s 103ms | 0h 7m 54s 772ms |
| 11/29/2020 9:03 | 47.96 | 47.6 | 42.9 | 6h 13m 28s 100ms | 8h 10m 2s 33ms | 5h 39m 40s 250ms | 7m 47s 225ms | 0h 7m 49s 135ms | 0h 7m 55s 212ms |
| 11/22/2020 9:06 | 44.72 | 46.6 | 42.4 | 5h 38m 27s | 6h 1m 34s 933ms | 5h 38m 24s 75ms | 7m 34s 92ms | 0h 7m 45s 457ms | 0h 8m 26s 248ms |
| 11/15/2020 7:29 | 50.21 | 47.3 | 42.3 | 6h 38m 11s | 6h 12m 12s 267ms | 5h 31m 2s 242ms | 7m 35s 822ms | 0h 7m 51s 775ms | 0h 8m 28s 659ms |

*FIG. 3*

| Date | Consistency_ST | Consistency_MT | Consistency_LT |
|---|---|---|---|
| 12/13/2020 8:23 | 6 | 6 | 6.00 |
| 12/6/2020 7:35 | 8 | 8 | 6.00 |
| 11/29/2020 9:03 | 6 | 6 | 5.67 |
| 11/22/2020 9:06 | 8 | 6 | 5.08 |
| 11/15/2020 7:29 | 6 | 6 | 5.69 |

*FIG. 4*

| Date | Variability_ST | Variability_MT | Variability_LT |
|---|---|---|---|
| 12/13/2020 8:23 | | 1 | 0.67 |
| 12/6/2020 7:35 | | 1 | 0.58 |
| 11/29/2020 9:03 | | 1 | 0.50 |
| 11/22/2020 9:06 | | 1 | 0.46 |
| 11/15/2020 7:29 | | 1 | 0.38 |

*FIG. 5*

| Date | Long Run Fraction ST | Long Run Fraction MT | Long Run Fraction LT |
|---|---|---|---|
| 12/13/2020 8:23 | 0.21 | 0.22 | 0.22 |
| 12/6/2020 7:35 | 0.24 | 0.22 | 0.22 |
| 11/29/2020 9:03 | 0.22 | 0.21 | 0.20 |
| 11/22/2020 8:06 | 0.20 | 0.21 | 0.19 |
| 11/15/2020 7:29 | 0.22 | 0.22 | 0.19 |

*FIG. 6*

| Table 1 - 12/13/2020 | |
|---|---|
| Distance ST | 47.07 |
| Distance MT | 48.2 |
| Distance LT | 46.8 |
| Intensity ST | 7m 43s 990ms |
| Intensity MT | 7m 49s 128ms |
| Intensity LT | 7m 53s 764ms |
| Consistency ST | 6 |
| Consistency MT | 6 |
| Consistency LT | 8 |

*FIG. 8A*

| Table 2 - 12/13/2020 | |
|---|---|
| Distance ST | 47.07 |
| Distance MT | 40.2 |
| Distance LT | 46.8 |
| Intensity ST | 7m 43s 990ms |
| Intensity MT | 7m 49s 128ms |
| Intensity LT | 7m 53s 764ms |
| Consistency ST | 6 |
| Consistency MT | 6 |
| Consistency LT | 6 |
| Variability ST | 1 |
| Variability MT | 1 |
| Variability LT | 0.67 |

*FIG. 8B*

| Table 3 - 12/13/2020 | |
|---|---|
| Distance ST | 47.07 |
| Distance MT | 48.2 |
| Distance LT | 46.8 |
| Intensity ST | 7m 43s 980ms |
| Intensity MT | 7m 49s 129ms |
| Intensity LT | 7m 53s 764ms |
| Consistency ST | 6 |
| Consistency MT | 8 |
| Consistency LT | 6 |
| Long Run Fraction ST | 0.21 |
| Long Run Fraction MT | 0.22 |
| Long Run Fraction LT | 0.22 |

FIG. 8C

| Table 4 - 12/13/2020 | |
|---|---|
| Distance ST | 47.07 |
| Distance MT | 48.2 |
| Distance LT | 48.8 |
| Intensity ST | 7m 43s 980ms |
| Intensity MT | 7m 49s 129ms |
| Intensity LT | 7m 59s 764ms |
| Consistency ST | 6 |
| Consistency MT | 8 |
| Consistency LT | 6 |
| Variability ST | 1 |
| Variability MT | 1 |
| Variability LT | 0.67 |
| Long Run Fraction ST | 0.21 |
| Long Run Fraction MT | 0.22 |
| Long Run Fraction LT | 0.22 |

FIG. 8D

| Time Period | STCon | MTCon | LTCon | STVar | MTVar | LTVar | STVol | MTVol | LTVol | Max Volume | STLvl | MTLvl | LTLvl | STPk | MTDvr | LTDvr | STPAr | MTPAr | LTPAr | Inlvl Label |
|---|---|---|---|---|---|---|---|---|---|---|---|---|---|---|---|---|---|---|---|---|
| 11/22/21 | 6 | 6 | 6 | 0 | 0 | 0.83 | 52.82 | 50.18 | 49.76 | 11.15 | 0.2111 | 0.148 | 0.1897 | 25441 | 22692 | 23363 | 482 | 471 | 469 | 0 |
| 11/15/21 | 6 | 6 | 6 | 1 | 0.67 | 0.92 | 48.03 | 50.15 | 48.39 | 8.02 | 0 | 0.1499 | 0.1832 | 21830 | 22469 | 23147 | 454 | 468 | 469 | 0 |
| 11/8/21 | 6 | 6 | 6 | 0 | 0.67 | 0.92 | 49.62 | 50.54 | 49.53 | 11.26 | 0.2869 | 0.2165 | 0.2023 | 23023 | 23774 | 23695 | 476 | 470 | 470 | 0 |
| 11/1/21 | 6 | 6 | 6 | 0 | 0.67 | 0.92 | 52.44 | 50.03 | 49.43 | 11.53 | 0.2198 | 0.2102 | 0.2006 | 24662 | 23446 | 23218 | 475 | 469 | 470 | 0 |
| . | . | . | . | . | . | . | . | . | . | . | . | . | . | . | . | . | . | . | . | . |
| 9/21/20 | 6 | 4.667 | 5.667 | 0 | 0 | 0.667 | 41.83 | 30.45 | 43.82 | 9.02 | 0.2151 | 0.0717 | 0.1901 | 20824 | 14876 | 20812 | 497 | 489 | 475 | 0 |
| 9/14/20 | 6 | 4.667 | 5.667 | 0 | 0.333 | 0.75 | 40.62 | 30.4 | 44.47 | 7.85 | 0 | 0.0674 | 0.1908 | 19350 | 14618 | 21087 | 476 | 481 | 474 | 0 |
| 9/7/20 | 2 | 4.667 | 5.667 | 0 | 0.333 | 0.75 | 8.6 | 33.48 | 44.8 | 4.67 | 0 | 0.1438 | 0.2064 | 4453 | 16167 | 21403 | 506 | 483 | 478 | 0 |
| 8/31/20 | 6 | 0 | 6 | 1 | 0.667 | 0.833 | 41.78 | 45.9 | 47.61 | 8.45 | 0.2022 | 0.2257 | 0.2249 | 20054 | 22117 | 22689 | 480 | 482 | 477 | 1 |
| 8/24/20 | 6 | 6 | 6 | 0 | 0.667 | 0.833 | 49.86 | 48.56 | 48.29 | 11.43 | 0.2592 | 0.232 | 0.226 | 23994 | 23306 | 22992 | 481 | 479 | 476 | 0 |
| . | . | . | . | . | . | . | . | . | . | . | . | . | . | . | . | . | . | . | . | . |
| 5/27/19 | 0 | 1 | 3.833 | 0 | 0 | 0.5 | 0 | 1.64 | 22.02 | 0 | 0 | 0 | 0.1469 | 0 | 630 | 10331 | 0 | 598 | 469 | 0 |
| 5/20/19 | 1 | 3 | 4.25 | 0 | 0.333 | 0.583 | 2.59 | 7.63 | 24.77 | 2.59 | 0 | 0 | 0.1704 | 1351 | 3852 | 11509 | 522 | 505 | 465 | 0 |
| 5/13/19 | 3 | 4 | 4.583 | 0 | 0.333 | 0.667 | 2.32 | 12.7 | 26.0 | 1.85 | 0 | 0 | 0.1932 | 1438 | 6121 | 12494 | 620 | 492 | 466 | 0 |
| 5/6/19 | 6 | 5 | 4.75 | 0 | 0.067 | 0.833 | 17.06 | 24.84 | 28.80 | 6.04 | 0 | 0.1218 | 0.1952 | 8766 | 11623 | 13393 | 486 | 486 | 464 | 0 |
| 4/29/19 | 4 | 4.667 | 4.867 | 1 | 1 | 0.917 | 17.8 | 27.74 | 30.8 | 6.02 | 0 | 0.1219 | 0.2256 | 8159 | 12869 | 14204 | 458 | 484 | 461 | 0 |
| 4/22/19 | 5 | 4.667 | 4.75 | 1 | 1 | 0.947 | 38.75 | 32.45 | 32.47 | 14.17 | 0.3657 | 0.2520 | 0.2545 | 17843 | 15116 | 14921 | 403 | 466 | 460 | 1 |
| 4/15/19 | 5 | 4.333 | 4.75 | 1 | 1 | 0.917 | 26.68 | 31.67 | 32.43 | 7.07 | 0 | 0.2412 | 0.2458 | 12504 | 14669 | 14872 | 466 | 463 | 459 | 0 |
| . | . | . | . | . | . | . | . | . | . | . | . | . | . | . | . | . | . | . | . | . |
| 7/23/18 | 5 | 4.333 | 4.833 | 1 | 0.667 | 0.917 | 35.48 | 25.08 | 32.04 | 12.01 | 0.3395 | 0.2235 | 0.2771 | 16270 | 11829 | 14692 | 459 | 472 | 459 | 0 |
| 7/16/18 | 5 | 4.333 | 4.75 | 2 | 0.667 | 1 | 24.4 | 24.69 | 31.6 | 0.1 | 0.332 | 0.2079 | 0.2486 | 11028 | 11513 | 14539 | 477 | 466 | 460 | 0 |
| 7/9/18 | 3 | 4.333 | 4.833 | 0 | 1 | 1.083 | 15.37 | 28.66 | 32.24 | 6.7 | 0 | 0.1976 | 0.2472 | 7678 | 13107 | 14745 | 493 | 457 | 457 | 0 |
| 7/2/18 | 5 | 5 | 5 | 1 | 1 | 1.167 | 34.31 | 36.78 | 33.09 | 10.01 | 0.2318 | 0.3249 | 0.2472 | 15333 | 16897 | 15079 | 447 | 451 | 456 | 0 |
| 6/25/18 | 5 | 4.667 | 5 | 0.667 | 1 | 1.167 | 30.29 | 33.9 | 33.24 | 12.01 | 0.3509 | 0.3635 | 0.261 | 16409 | 15998 | 16211 | 452 | 454 | 458 | 1 |
| . | . | . | . | . | . | . | . | . | . | . | . | . | . | . | . | . | . | . | . | . |
| 1/29/18 | 6 | 5 | 4.833 | 1 | 1 | 0.917 | 36.95 | 33.83 | 34.16 | 12.04 | 0.3258 | 0.2784 | 0.3592 | 17561 | 15380 | 15405 | 475 | 457 | 451 | 0 |
| 1/22/18 | 5 | 4.667 | 4.75 | 2 | 1 | 0.947 | 35.9 | 32.98 | 33.92 | 8 | 0.2335 | 0.2846 | 0.3575 | 15893 | 14970 | 15241 | 444 | 455 | 449 | 0 |
| 1/15/18 | 4 | 4 | 4.667 | 0 | 0.667 | 0.833 | 28.13 | 31.17 | 33.71 | 6.04 | 0.2656 | 0.3015 | 0.3686 | 12696 | 14221 | 15178 | 451 | 456 | 450 | 0 |
| 1/8/18 | 5 | 4.333 | 4.833 | 1 | 0.667 | 1 | 34.72 | 32.77 | 34.21 | 13 | 0.3744 | 0.3961 | 0.3695 | 16321 | 14876 | 15413 | 470 | 454 | 451 | 0 |
| 1/1/18 | 3 | 4.333 | 4.833 | 1 | 0.667 | 1 | 30.85 | 34.16 | 33.85 | 13 | 0.4241 | 0.3899 | 0.363 | 13645 | 15177 | 15311 | 445 | 444 | 452 | 0 |

*FIG. 11*

| Short-Term Metric | Limitation | 8/31/2020 Data | Short-Term Metric Adjusted Value Range |
|---|---|---|---|
| Volume | 2 times value | 41.78 mi | 41.78 - 83.56 mi |
| Long Run Fraction | 2 times value | 0.2022 | 0.2022 - 0.4044 |
| Consistency | Value plus 2 | 6 | 6 - 8 |
| Variability | Value plus 2 | 1 | 1 - 3 |
| Intensity | 20% increase of value | 480 sec/mi (7.5 mph) | 480 - 384 sec/mi (7.5 - 9.38 mph) |

*FIG. 12*

```
df_augment = df3
for i in range(1,70):
    n = np.random.rand()
    # Adjusting 8/31/2020 Injury @ Row 32 in Data frame (df_augment)
    new_row1 = df3.loc[[32],:]
    # Adjust a value in one of the columns
    if n < 0.2:
        new_row1.iloc[0,7] = new_row1.iloc[0,7] * (1 + np.random.rand()) # adjusting ST Volume in column 7 (up to 2x)
    elif 0.2 < n < 0.4:
        new_row1.iloc[0,11] = new_row1.iloc[0,11] * (1 + np.random.rand()) # adjusting ST Long Run Fraction in column 11 (up to 2x)
    elif 0.4 < n < 0.6:
        new_row1.iloc[0,1] = new_row1.iloc[0,1] + (1 + np.random.randint(2)) # adjusting ST Consistency in column 1 (up to +2)
    elif 0.6 < n < 0.8:
        new_row1.iloc[0,4] = new_row1.iloc[0,4] + (1 + np.random.randint(2)) # adjusting ST Variability in column 4 (up to +2)
    else:
        new_row1.iloc[0,17] = new_row1.iloc[0,17] * n # adjusting ST Pace in column 17 (up to 20% higher intensity)

# Appending new row to main data frame (df)
    df_augment = df_augment.append(new_row1)
```

*FIG. 13*

| Time Period | LTCon | LTDcr | LTLcf | LTPac | LTYer | LTVol | MTCon | MTDcr | MTLcf | MTPac | MTYer | MTVol | Max_Volume | STSCon | STDcr | STLcf | STPac | STYer | STVol | Injury_Label |
|---|---|---|---|---|---|---|---|---|---|---|---|---|---|---|---|---|---|---|---|---|
| 11/22/21 | 0.8420 | 1.1127 | -0.7512 | 0.3822 | 0.1731 | 1.0708 | 0.8468 | 1.0058 | -0.3844 | 0.1752 | -0.2784 | 0.8534 | 0.1710 | 0.5930 | 1.2810 | -0.1212 | 0.3274 | -1.3382 | 1.1142 | 0 |
| 11/15/21 | 0.8420 | 1.0807 | -0.7435 | 0.3002 | 0.5590 | 1.0302 | 0.6468 | 0.9668 | -0.9897 | 0.0906 | -0.2784 | 0.9495 | -0.8170 | 0.5630 | 0.5682 | -1.8909 | -0.1207 | 0.3782 | 0.8803 | 0 |
| 11/8/21 | 0.8420 | 1.0963 | -0.4460 | 0.4961 | 0.5590 | 1.0460 | 0.8468 | 1.0361 | -0.1298 | 0.1470 | -0.2784 | 0.9892 | 0.2067 | 0.5630 | 0.9218 | 0.0113 | 0.2314 | 0.3782 | 0.8207 | 0 |
| 11/1/21 | 0.8420 | 1.0778 | -0.4724 | 0.4861 | 0.5590 | 1.0347 | 0.8468 | 0.9662 | -0.2040 | 0.1166 | -0.2784 | 0.9386 | 0.2910 | 0.5630 | 1.1726 | -0.0474 | 0.2154 | -1.5562 | 1.0798 | 0 |
| 10/26/21 | 0.8420 | 1.0279 | -0.7575 | 0.3522 | 1.4420 | 0.9986 | 0.8468 | 0.8692 | -0.3917 | 0.0061 | 0.5591 | 0.5788 | -0.1795 | 0.5630 | 0.7608 | -0.1924 | -0.0247 | 0.3782 | 0.8182 | 0 |

FIG. 14

| Artificial Neural Network (ANN) | AUC - Training Data | AUC - Test Data |
|---|---|---|
| 12 Inputs (Volume, Intensity, Consistency, LRF) | | |
| ANN with 12/4/1 nodes per layer | 0.9927 | 0.9865 |
| ANN with 12/4/2/1 nodes per layer | 1.0000 | 1.0000 |
| ANN with 12/8/1 nodes per layer | 0.9991 | 0.9950 |
| ANN with 12/8/4/1 nodes per layer | 1.0000 | 0.9947 |
| ANN with 12/12/3/1 nodes per layer | 1.0000 | 1.0000 |
| ANN with 12/12/6/1 nodes per layer | 1.0000 | 1.0000 |
| 9 Inputs (Volume, Intensity, Consistency) | | |
| ANN with 9/3/1 nodes per layer | 0.9058 | 0.8516 |
| ANN with 9/3/2/1 nodes per layer | 0.9759 | 0.9633 |
| ANN with 9/6/1 nodes per layer | 0.9754 | 0.9180 |
| ANN with 9/6/3/1 nodes per layer | 0.9887 | 0.9730 |
| ANN with 9/4/2/1 nodes per layer | 0.9786 | 0.9295 |
| 6 Inputs (Volume, Intensity) | | |
| ANN with 6/2/1 nodes per layer | 0.7577 | 0.7465 |
| ANN with 6/6/3/1 nodes per layer | 0.8933 | 0.8707 |
| ANN with 6/4/2/1 nodes per layer | 0.5000 | 0.5000 |

FIG. 15

| | |
|---|---|
| Input Layer | 12 nodes |
| Hidden Layer (1) | 4 nodes |
| Hidden Layer (2) | 2 nodes |
| Output Layer | 1 node |
| Learning Rate | 0.001 |
| Epochs | 200 |
| Batch Size | 16 |
| Train/Test Split | 80% / 20% |

*FIG. 16*

| | Instance Data 03/21/2022 | Scaled Data |
|---|---|---|
| LTCon | 5.917 | 0.7320 |
| LTLrf | 0.2266 | -0.0675 |
| LTPac | 473 | 0.8457 |
| LTVol | 52.2 | 1.3472 |
| MTCon | 6 | 0.6468 |
| MTLrf | 0.1663 | -0.7445 |
| MTPac | 479 | 0.4007 |
| MTVol | 51.41 | 1.0757 |
| STCon | 6 | 0.5630 |
| STLrf | 0.2632 | 0.3156 |
| STPac | 468 | 0.1033 |
| STVol | 57 | 1.4976 |

FIG. 19A

```
Input: tf.Tensor(
[[ 0.732 -0.0675  0.8457  1.3472  0.6468 -0.7445  0.4007  1.0757  0.563
   0.3156  0.1033  1.4976]], shape=(1, 12), dtype=float64)

Prediction:0 = injury free / 1 = injury

Output: [[0.]]
Keep on keeping on
```

FIG. 19B

| | Inference Data (unscaled) | Scaled Data |
|---|---|---|
| LTCon | 5.917 | 0.7320 |
| LTLrf | 0.2324 | 0.0229 |
| LTPac | 476 | 1.1933 |
| LTVol | 53.1 | 1.4488 |
| MTCon | 6 | 0.6468 |
| MTLrf | 0.2732 | 0.5716 |
| MTPac | 484 | 0.5417 |
| MTVol | 57.84 | 1.7151 |
| STCon | 6 | 0.5630 |
| STLrf | 0.3083 | 0.6937 |
| STPac | 479 | 0.2794 |
| STVol | 60 | 1.7728 |

*FIG. 20A*

```
Input: tf.Tensor(
[[0.732  0.0229 1.1933 1.4488 0.6468 0.5716 0.5417 1.7151 0.563  0.6937
  0.2794 1.7728]], shape=(1, 12), dtype=float64)

Prediction:0 = injury free / 1 = injury

Output: [[1.]]
Whoa! Watch out!
```

*FIG. 20B*

| | Reference Data (09/28/2022) | Subject Data |
|---|---|---|
| LTCon | 5.833 | 0.6206 |
| LTLrf | 0.2391 | 0.1272 |
| LTPac | 476 | 1.1933 |
| LTVol | 52.06 | 1.3314 |
| MTCon | 5.667 | 0.2953 |
| MTLrf | 0.3002 | 0.9040 |
| MTPac | 484 | 0.5417 |
| MTVol | 53.68 | 1.3014 |
| STCon | 5 | -0.3632 |
| STLrf | 0.3895 | 1.3744 |
| STPac | 479 | 0.2794 |
| STVol | 47.5 | 0.6262 |

FIG. 21A

```
Input: tf.Tensor(
[[ 0.6206  0.1272  1.1933  1.3314  0.2953  0.904   0.5417  1.3014 -0.3632
   1.3744  0.2794  0.6262]], shape=(1, 12), dtype=float64)

Prediction:0 = injury free / 1 = injury

Output: [[0.]]
Keep on keeping on
```

FIG. 21B

PREDICTING RISK OF RUNNING-RELATED INJURY USING A MACHINE LEARNING MODEL AND RELATED MACHINE LEARNING TRAINING METHODS

CROSS REFERENCE TO RELATED APPLICATIONS

This application claims priority to U.S. provisional application No. 63/174,506, filed Apr. 13, 2021, titled "PREDICTING RISK OF RUNNING-RELATED INJURY USING A MACHINE LEARNING MODEL," the disclosure of which is incorporated herein by reference in its entirety.

BACKGROUND

Running is a popular activity. For example, in the United States, millions of people maintain fitness by running on a regular basis. Running, however, poses a high risk of injury due to the repetitive stress on the runner's body. By some estimates, more than 50 percent of runners experience an injury each year. During time off, runners lose fitness, miss opportunities, and experience adverse physical and mental health effects. Unfortunately, preventing injuries is an extremely difficult task. In fact, conventional injury preventive measures are often either subjective (e.g., listen to your body) or rules of thumb (e.g., avoid a week-to-week mileage increase of greater than 10%). These conventional prevention methods are also inaccurate. Moreover, researchers have not yet uncovered any predictive characteristics (e.g., strength, flexibility, biomechanics, injury history, etc.) to identify which runners are likely to get injured and/or why so. See Hutchinson, Alex, The Elusive Art of Predicting Injuries, Outside Online.com, published May 7, 2021, https://www.outsideonline.com/2423442/running-injuries-prediction-research (accessed May 8, 2021). There is therefore a need in the art for tools to predict running-related injuries.

SUMMARY

An example machine learning-based method for predicting risk of running-related injury is described herein. The method includes receiving a runner profile, inputting the runner profile into a trained machine learning model, and predicting, using the trained machine learning model, a risk of musculoskeletal injury based on the runner profile. The runner profile includes at least one volume metric, at least one intensity metric, and at least one consistency metric.

Additionally, in some implementations, the at least one volume metric includes one or more of a daily run volume metric, a short-term run volume metric, a medium-term run volume metric, and a long-term run volume metric. The at least one volume metric can be running duration or distance data.

Alternatively or additionally, in some implementations, the at least one intensity metric includes one or more of a daily run intensity metric, a short-term run intensity metric, a medium-term run intensity metric, and a long-term run intensity metric.

Alternatively or additionally, in some implementations, the at least one consistency metric includes one or more of a short-term consistency metric, a medium-term consistency metric, and a long-term consistency metric.

Optionally, in some implementations, the runner profile further includes at least one variability metric. The at least one variability metric includes one or more of a short-term variability metric, a medium-term variability metric, and a long-term variability metric.

Optionally, in some implementations, the runner profile further includes at least one long run fraction metric. The at least one long run fraction metric includes one or more of a short-term long run fraction metric, a medium-term long run fraction metric, and a long-term long run fraction metric.

Optionally, in some implementations, the runner profile further includes at least one dynamic metric.

Optionally, in some implementations, the runner profile further includes a physiological metric. The physiological metric can be heart rate data, oxygen saturation data, or $VO_2$ max data.

Optionally, in some implementations, the prediction is a probability of musculoskeletal injury. In other implementations, the prediction is a classification into a risk category.

In some implementations, the machine learning model is a supervised learning model or a semi-supervised learning model. For example, the machine learning model can be a logistic regression model, a support vector machine, or an artificial neural network. Optionally, the machine learning model is a deep learning model.

An example machine learning-based system for predicting risk of running-related injury is also described herein. The system includes a trained machine learning model, and a computing device. The computing device includes a processor and a memory, the memory having computer-executable instructions stored thereon. The computing device is configured to receive a runner profile, input the runner profile into the trained machine learning model, and receive, from the trained machine learning model, a risk of musculoskeletal injury. The trained machine learning model predicts the risk of musculoskeletal injury based on the runner profile. The runner profile includes at least one volume metric, at least one intensity metric, and at least one consistency metric.

An example method for training a machine learning model is also described herein. The method includes receiving a dataset including running-related data, where the running-related data includes a plurality of samples tagged with respective running-related injury labels. The method also includes augmenting the dataset, where the augmented dataset further includes a plurality of synthetic samples tagged with respective running-related injury labels. The method further includes training a machine learning model using the augmented dataset. The trained machine learning model is configured for predicting risk of running-related injury.

In some implementations, the step of augmenting the dataset includes creating the plurality of synthetic samples from the running-related data. For example, a synthetic sample is created by adjusting a value of at least one metric associated with a sample tagged with an injury state label. Optionally, the step of augmenting the dataset further includes imposing a knowledge-based limitation on the adjusted value of the at least one metric associated with the sample tagged with the injury state label.

Alternatively or additionally, in some implementations, the running-related data includes at least one volume metric, at least one intensity metric, at least one consistency metric, at least one long run fraction metric, or at least one variability metric. Optionally, in some implementations, the running-related data includes the at least one volume metric, the at least one intensity metric, the at least one consistency metric, and the at least one long run fraction metric. Additionally, the running-related data optionally further includes at least one dynamic metric. Alternatively or additionally, the running-related data optionally further includes at least one physiological metric.

In some implementations, the dataset includes respective running-related data associated with a plurality of runners. Alternatively, in other implementations, the dataset includes running-related data associated with a single runner.

Alternatively or additionally, the at least one volume metric includes one or more of a short-term volume metric, a medium-term volume metric, and a long-term volume metric. Alternatively or additionally, the at least one intensity metric includes one or more of a short-term intensity metric, a medium-term intensity metric, and a long-term intensity metric. Alternatively or additionally, the at least one consistency metric includes one or more of a short-term consistency metric, a medium-term consistency metric, and a long-term consistency metric. Alternatively or additionally, the at least one long run fraction metric includes one or more of a short-term long run fraction metric, a medium-term long run fraction metric, and a long-term long run fraction metric. Alternatively or additionally, the at least one variability metric includes one or more of a short-term variability metric, a medium-term variability metric, and a long-term variability metric.

In some implementations, the trained machine learning model is configured to predict risk of running-related injury by classifying a runner profile into one of a plurality of risk categories. In other implementations, the trained machine learning model is configured to predict risk of running-related injury by providing a probability of musculoskeletal injury for a runner profile.

In some implementations, the step of training the machine learning model includes minimizing or maximizing an objective function. Optionally, the objective function is an error between the machine learning model's running-related injury risk prediction and ground truth.

In some implementations, the method optionally further includes evaluating performance of the trained machine learning model using an accuracy measure such as an F-score or area under the receiver operator curve (AUC).

In some implementations, the method optionally further includes preprocessing the dataset or the augmented dataset. For example, the step of preprocessing can include data feature scaling.

In some implementations, the machine learning model is a deep learning model. For example, the deep learning model is an artificial neural network.

An example method for predicting risk of running-related injury is also described herein. The method includes training a machine learning model as described above. The method also includes inputting a runner profile into the trained machine learning model; and predicting, using the trained machine learning model, a risk of musculoskeletal injury, where the trained machine learning model is configured to predict risk of running-related injury.

In some implementations, the runner profile includes at least one volume metric, at least one intensity metric, at least one consistency metric, at least one long run fraction metric, at least one variability metric, at least one dynamic metric, or at least one physiological metric. Optionally, the runner profile includes the at least one volume metric, the at least one intensity metric, the at least one consistency metric, and the at least one long run fraction metric.

In some implementations, the risk of musculoskeletal injury is a classification into one of a plurality of risk categories. In other implementations, the risk of musculoskeletal injury is a probability of musculoskeletal injury.

In some implementations, the machine learning model is a deep learning model.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 2A is a table illustrating example running-related data according to an implementation described herein. FIG. 2B is a table illustrating example running-related data that is grouped by week according to an implementation described herein.

FIG. 3 is a table illustrating example volume and intensity metrics according to an implementation described herein.

FIG. 4 is a table illustrating example consistency metrics according to an implementation described herein.

FIG. 5 is a table illustrating example variability metrics according to an implementation described herein.

FIG. 6 is a table illustrating example long run fraction metrics according to an implementation described herein.

FIGS. 8A-8D are tables illustrating example machine learning model features according to implementations described herein. The table of FIG. 8A includes volume, intensity, and consistency metrics. The table of FIG. 8B includes volume, intensity, consistency, and variability metrics. The table of FIG. 8C includes volume, intensity, consistency, and long run fraction metrics. The table of FIG. 8D includes volume, intensity, consistency, variability, and long run fraction metrics.

FIG. 11 is an excerpt from an example labeled dataset including running-related data for one individual runner according to an implementation described herein.

FIG. 12 is a table of example knowledge-based limitations used for creating synthetic data according to an implementation described herein.

FIG. 13 is example pseudocode for creating a synthetic sample according to an implementation described herein.

FIG. 14 is an excerpt from an example augmented labeled dataset after data scaling according to an implementation described herein.

FIG. 15 is a table illustrating an area under the receiver operating curve (AUC) analysis for a plurality of machine learning models trained using a scaled, augmented dataset (e.g., FIG. 14) according to an implementation described herein.

FIG. 16 is a table illustrating example feedforward artificial neural network (ANN) architecture and hyperparameters according to an implementation described herein. The example ANN was trained using a scaled, augmented dataset (e.g., FIG. 14). The ANN has 12 input nodes for receiving short-, medium-, and long-term metrics for each of volume, intensity, consistency, and long run fraction (i.e., the model "features").

FIG. 19A is a table illustrating raw and scaled inference data associated with an example training plan for the week of Feb. 21, 2022. FIG. 19B illustrates the model input and output associated with the inference data of FIG. 19A. The model is the trained ANN of FIG. 16.

FIG. 20A is a table illustrating raw and scaled inference data associated with an example training plan for the week of Feb. 28, 2022. FIG. 20B illustrates the model input and output associated with the inference data of FIG. 20A. The model is the trained ANN of FIG. 16.

FIG. 21A is a table illustrating raw and scaled inference data associated with an alternative example training plan for the week of Feb. 28, 2022. FIG. 21B illustrates the model input and output associated with the inference data of FIG. 21A. The model is the trained ANN of FIG. 16.

DETAILED DESCRIPTION

Figure 1:
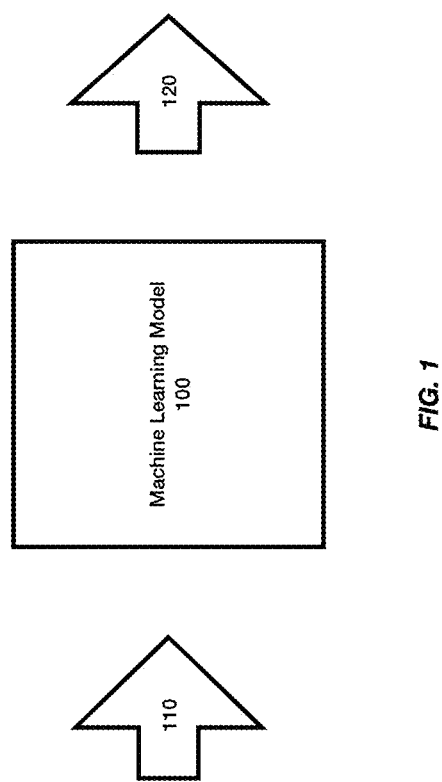
FIG. 1 is a block diagram illustrating a machine learning model operating in inference mode according to an implementation described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. As used herein, the terms "about" or "approximately" when referring to a measurable value such as an amount, a percentage, and the like, is meant to encompass variations of ±20%, ±10%, ±5%, or ±1% from the measurable value. While implementations will be described for predicting musculoskeletal injury in a runner using an artificial neural network, it will become evident to those skilled in the art that the implementations are not limited thereto, but are applicable for providing predictions with other supervised or semi-supervised machine learning models.

Described herein are machine learning-based systems and methods for predicting risk of musculoskeletal injury in a runner. As noted above, runners are at high risk of injury due, at least in part, to the repetitive stress running imposes on the human body. For example, more than 50% of runners (~80% according to some estimates) experience an injury each year. This is particularly true for long distance runners. The machine learning-based systems and methods described herein can predict risk of musculoskeletal injury based on patterns present in running-related data. For example, the interrelationship between running volume, intensity, consistency, variability, fractional contribution of long run, and other characteristics is highly complex. Machine learning is a technical tool that is capable of analyzing complex data and identifying patterns in data. As described herein, the machine learning-based systems and methods analyze the interrelationship between running volume, intensity, fractional long run contribution, and consistency (and optionally in some implementations, variability, dynamics, and/or physiology) in a runner's data. According to this disclosure, analyzing, using a machine learning model, a runner's consistency, variability, long runs, or combinations thereof in addition to the runner's volume and intensity can provide information predictive of injury. Thus, the machine learning-based systems and methods described herein provide improvements over conventional injury prevention measures, which are inaccurate at best, subjective, and/or merely rule of thumb. Unlike the technical solutions described herein, conventional techniques cannot identify which combination of relative change in running volume, intensity, and consistency (or variability, long run fraction, or other feature) leads to an increased injury risk. For example, it is not uncommon for even an experienced runner to sustain an injury despite "listening to his body" and carefully managing changes in training (e.g., volume, intensity, etc.). In contrast, the machine learning-based systems and methods described herein approach the problem in a technical manner and are thus capable of finding patterns in a runner's data and predicting risk of injury (see Examples below). The improved injury prevention techniques of this disclosure therefore facilitate better training outcomes and also keep runners active, which has positive impact on both physical and mental health of the runner. The systems and methods described herein also facilitate a runner's ability to optimize the volume and intensity of training while at the same time lowering risk of injury. Moreover, the machine learning model training methods described herein provide solutions to technical problems presented by running-related datasets. Such solutions include, but are not limited to, data augmentation in a matter tailored specifically to running-related data, for example, by imposing knowledge-based limitations on creation of synthetic data.

As used herein, musculoskeletal injuries affect a runner's bones, joints, or soft tissues such as muscles, tendons, ligaments, or other connective tissue. Running-related injuries include, but are not limited to, those affecting the feet, knees, upper or lower legs, hips, pelvis, or groin. Example running-related musculoskeletal injuries include, but are not limited to, stress fractures, tendonitis, plantar fasciitis, iliotibial (IT) band syndrome, strains, and sprains. Additionally, this disclosure contemplates that a musculoskeletal injury forces a runner to rest (not run) for an extend period of time (e.g., from 3-5 days or longer such as several weeks, months, or even longer). Thus, as used herein, a running-related injury results in a runner taking 3 or more consecutive days of rest. It has been shown that a human's bones and muscles weaken as a result of inactivity. Thus, ramping up training post-injury is known to be associated with higher risk of injury.

Referring now to FIG. 1, a block diagram illustrating a machine learning model 100 is shown. In FIG. 1, the machine learning model 100 is operating in inference mode. In other words, the machine learning model 100 has already been trained with a data set (or "dataset"). This disclosure contemplates that the machine learning model 100 is a supervised learning model. According to supervised learning, the machine learning model 100 "learns" a function that maps an input 110 (sometimes referred to herein as the "features") to an output 120 (sometimes referred to herein as the "target") based on a data set, which includes a plurality of samples (e.g., the model input, features, or runner profile described herein) tagged with one or more labels (e.g., the injury/no injury tags described herein), during model training mode. It should be understood that supervised learning is provided only as an example. This disclosure contemplates that the machine learning model 100 may be a semi-supervised learning model in some implementations. Semi-supervised learning models are trained with a data set including both labeled data as well as unlabeled data.

The machine learning model 100 shown in FIG. 1 can be an artificial neural network. Optionally, the machine learning model 100 is a deep neural network, which includes multiple hidden layers between the input and output layers (described below). An artificial neural network is a computing system including a plurality of interconnected neurons (e.g., also referred to as "nodes"). This disclosure contemplates that the nodes can be implemented using a computing device (e.g., a processing unit and memory as described herein). The nodes can optionally be arranged in a plurality of layers such as input layer, output layer, and one or more hidden layers. Each node is connected to one or more other nodes in the artificial neural network. For example, each layer has a plurality of nodes, where each node is connected to all nodes in the previous layer. The nodes in a given layer are not interconnected with one another, i.e., the nodes in a given layer function independently of one another. As used herein, nodes in the input layer receive data (sometimes referred to herein as the "features" or input 110) from outside of the artificial neural network, nodes in the hidden layer(s) modify the data between the input and output layers, and nodes in the output layer provide the results (sometimes referred to herein as the "target" or output 120).

Each node in the artificial neural network is configured to receive an input and implement a function (sometimes referred to herein as the "activation function"). In other words, the activation function defines the node output for a given input. Activation functions include, but are not limited to, binary step, sigmoid, tanh, and rectified linear unit (ReLU). Additionally, each node is associated with a respective weight. Artificial neural networks are trained with a data set to minimize or maximize an objective function, which is a measure of the artificial neural network's performance. The objective function may be a cost function. Cost functions include, but are not limited to, mean squared error (MSE), mean absolute error, L1 loss (least absolute deviations), L2 loss (least squares loss), and cross-entropy loss. Training algorithms for artificial neural networks include, but are not limited to, backpropagation (BP). The training algorithm tunes the node weights and/or bias to minimize or maximize the objective function. For example, BP involves computing the gradient of the objective function with respect to the respective weights for each of the nodes. It should be understood that any algorithm that finds the minimum or maximum of the objective function can be used to for training an artificial neural network. Although artificial neural networks are provided as an example, this disclosure contemplates that the machine learning model 100 can be other types of models including, but not limited to, a logistic regression model or a support vector machine.

As described above, the machine learning model 100 is trained to map the input 110 to the output 120. In the examples described herein, the input 110 is a runner profile, and the output 120 is a risk of musculoskeletal injury, e.g., running-related musculoskeletal injury. As used herein, the risk of musculoskeletal injury can be a classification (e.g., injury or no injury) in some implementations or a predicted risk value (e.g., regression) in other implementations. As described above, musculoskeletal injuries affect a runner's bones, joints, or soft tissues and also force the runner to rest for an extended time period. The runner profile includes one or more "features" that are input into the machine learning model 100, which predicts risk of musculoskeletal injury based on the features. The risk of musculoskeletal injury is therefore the "target" of the machine learning model 100.

This disclosure contemplates that the features of the runner profile can be obtained from a runner's log, e.g., the record used to track running-related information such as mileage, running duration, physiological data, environmental conditions, injuries, or other information related to running. Optionally, the runner's log is maintained in an electronic medium. For example, Internet-based services for tracking fitness data are in common use by runners. Example Internet-based services include, but are not limited to, the STRAVA mobile app and website of Strava, Inc. of San Francisco, Calif. and GARMIN CONNECT mobile app and website of Garmin International of Olathe, Kans. It should be understood that the STRAVA and GARMIN CONNECT mobile apps and websites are provided only as example Internet-based services. This disclosure contemplates that other electronic and/or Internet-based services may be used to track running-related data.

Internet-based services maintain a vast amount of running-related data for a plurality of runners. For example, the STRAVA mobile app and website currently (year 2021) has approximately 76 million users. Running-related data includes, but is not limited to, global positioning system (GPS) route data (e.g., XML format files such as GPX or TCX files); mileage; duration; pace; speed; sensor data (e.g., heart rate monitor, accelerometer, etc.); dynamic data (e.g., cadence, stride length); perceived effort; and free-form comments. Such running-related data is primarily measured using a device, for example, a running watch, fitness tracker, or mobile phone. These devices include built-in location service such as GPS and, optionally, built-in or external sensors. An example running watch is the GARMIN FORERUNNER watch of Garmin International of Olathe, Kans. It should be understood that the GARMIN FORERUNNER watch is provided only as an example. This disclosure contemplates that other devices may be used to measure running-related data. Alternatively or additionally, running-related data may be entered or altered by the runner.

Figure 2A:
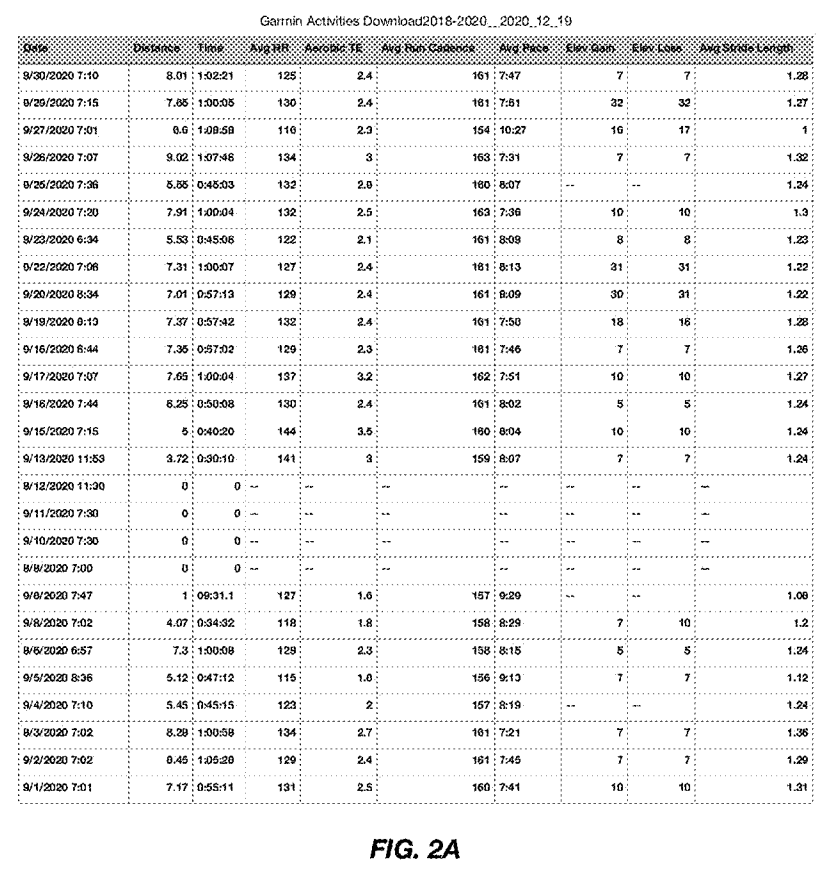

FIG. 2A is a table illustrating example raw running-related data for an example runner for the month of September 2020. The running-related data was downloaded from an Internet-based runner's log. The features input into the machine learning model 100 (i.e., the input 110) can include, but are not limited to, volume metrics (e.g., "Distance", "Time" in FIG. 2A), intensity metrics (e.g., "Avg Pace" in FIG. 2A), consistency metrics, variability metrics, long run fraction metrics, dynamic metrics (e.g., "Avg Stride Length" in FIG. 2A), and/or physiological metrics (e.g., "Avg HR" in FIG. 2A). As described herein, the features are taken and/or derived from the running-related data. The target predicted by the machine learning model 100 (i.e., the output 120) is a risk of musculoskeletal injury. Optionally, this disclosure contemplates that the running-related data may be tagged with a type of musculoskeletal injury (e.g., hip, knee, ankle, foot, tendon, ligament, etc.). Additionally, it should be understood that running-related data can be downloaded or exported from Internet-based service runner logs, for example, as a comma separated value (CSV) file, an XLS file, or other format file.

FIG. 2B is a table illustrating example raw running-related data that is grouped by week for the example runner for the months of August and September 2020. The running-related data was downloaded from an Internet-based runner's log. The features input into the machine learning model 100 (i.e., the input 110) can include, but are not limited to, volume metrics (e.g., "Total Distance", "Total Activity Time" in FIG. 2B), intensity metrics (e.g., average pace or speed derived from "Total Distance", "Total Activity Time" in FIG. 2B), consistency metrics (e.g., derived from "Activities" in FIG. 2B), variability metrics, long run fraction metrics (e.g., derived from "Total Distance", "Max Distance" in FIG. 2B), dynamic metrics, and/or physiological metrics. As described herein, the features are taken and/or derived from the running-related data. The target predicted by the machine learning model 100 (i.e., the output 120) is a risk of musculoskeletal injury. As shown in FIG. 2B, the running-related data includes a column for labelling or tagging injuries (e.g., "Injury Label" in FIG. 2B). In FIG. 2B, label '1' indicates an injured state (sometimes also referred to herein as "injury state"), and label '0' indicates an uninjured state (sometimes also referred to herein as "non-injury state" or "non-injured state"). In the example of FIG. 2B, the runner sustained a musculoskeletal injury during the week of Aug. 31, 2020. The labelling results in samples (e.g., the model input or runner profile described herein) tagged with one or more labels (e.g., Injury Labels) for machine learning model training. Optionally, this disclosure contemplates that the running-related data may be tagged with a type of musculoskeletal injury (e.g., hip, knee, ankle, foot, tendon, ligament, etc.). Additionally, it should be understood that running-related data can be downloaded or exported from Internet-based service runner logs, for example, as a comma separated value (CSV) file, an XLS file, or other format file.

It should be understood that a runner's device (e.g., running watch) can be operably connected to a computing device (e.g., using low-power wireless protocol such as BLUETOOTH or WiFi) such that data can be transferred to the Internet-based service. Data transfer can be accomplished on a periodic basis (e.g., daily). The Internet-based service maintains the running-related data, which is aggregated over time (e.g., weekly, monthly, yearly, etc.) allowing the runner to track fitness, progress, training, and goals.

As described below, metrics are provided for short-term, medium-term, and long-term periods. As used herein, a short-term period represents a training period. A training period can optionally be a 7 day period (e.g., a calendar week). It should be understood that a training period may be more or less than 7 days (e.g., a 10-day or 5-day period). It should also be understood that the training period length can be selected by a runner. As used herein, a medium-term period includes a plurality of training periods. The number of training periods in a medium-term period is selected to create metrics representing the transient fitness level of and stress on the runner. For example, the medium-term period can be a 2-4 week period (i.e., 2-4, 7-day training periods). It should be understood that 2-4 weeks is only provided as an example. As used herein, a long-term period includes a plurality of training periods, which is greater than the number of training periods of the medium-term period. The number of training periods in a long-term period is selected to create metrics representing the base fitness level of and stress on the runner. For example, the long-term period can be a 12-24 week period (i.e., 12-24, 7-day training periods). It should be understood that 12-24 weeks is only provided as an example.

A runner profile includes at least one volume metric. Volume metrics include, but are not limited to, a daily volume metric, a short-term volume metric, a medium-term volume metric, and a long-term volume metric. Optionally, in some implementations, the volume metrics includes a short-term volume metric, a medium-term volume metric, and a long-term volume metric. This disclosure contemplates that a volume metric is a measure of running time or duration (e.g., hours, minutes, seconds) and/or running distance (e.g., miles, kilometers). Additionally, this disclosure contemplates that the volume metrics can be obtained (e.g., received, downloaded, etc.) and/or derived from the electronic runner's log described above. As used herein, a daily volume metric is a 1-day cumulative run length (e.g., daily total), which can optionally include one or more runs. As used herein, a short-term volume metric is the cumulative run length during a training period. Additionally, as described above, a training period can optionally be a 7 day period (e.g., a calendar week). It should be understood that a training period may be more or less than 7 days (e.g., a 10-day or 5-day period). As used herein, a medium-term volume metric is an average cumulative run length over a plurality of training periods, for example, the average training period (e.g., weekly) run length over a 2-4 week period. It should be understood that 2-4 weeks is only provided as an example medium-term period. As used herein, a long-term volume metric is an average cumulative run length over a plurality of training periods, for example, the average training period (e.g., weekly) run length over a 12-24 week period. It should be understood that 12-24 weeks is only provided as an example long-term period. The short-, medium-, and long-term volume metrics represent cumulative run lengths over progressively longer periods of time. Additionally, as described above, run length can be measured by a duration and/or a distance.

A runner profile also includes at least one intensity metric. Intensity metrics include, but are not limited to, a daily intensity metric, a short-term intensity metric, a medium-term intensity metric, and a long-term intensity metric. Optionally, in some implementations, the intensity metrics includes a short-term intensity metric, a medium-term intensity metric, and a long-term intensity metric. This disclosure contemplates that an intensity metric is a running pace or running speed. Pace is measured as a time per distance unit (e.g., minutes per mile or minutes per kilometer). Speed is measured as distance per unit time (e.g., miles per hour or kilometers per hour). Additionally, this disclosure contemplates that the intensity metrics can be obtained (e.g., received, downloaded, etc.) and/or derived from the electronic runner's log described above. As used herein, a daily intensity metric is a 1-day average intensity (e.g., pace or speed). As used herein, a short-term intensity metric is the average intensity (e.g., pace or speed) during a training period. As used herein, a medium-term intensity metric is the average intensity (e.g., pace or speed) over a plurality of training periods. As used herein, a long-term intensity metric is the average intensity (e.g., pace or speed) over a plurality of training periods. The daily, short-, medium-, and long-term intensity metrics represent average intensity over progressively longer periods of time. Additionally, as described above, run intensity can be measured by pace or speed.

FIG. 3 is a table illustrating short-term, medium-term, and long-term volume and intensity metrics. For example, the table includes short-term volume metrics ("Distance ST", "Time ST"), medium-term volume metrics ("Distance MT", "Time MT"), and long-term volume metrics ("Distance LT", "Time LT") for an example runner during five consecutive weeks in November and December of 2020. The table also includes short-term intensity metrics ("Intensity ST"), medium-term intensity metrics ("Intensity MT"), and long-term intensity metrics ("Intensity LT") for the example runner during five consecutive weeks in November and December of 2020. In FIG. 3, the short-term, medium-term, and long-term periods are 1, 3, and 12 weeks, respectively. As described above, these lengths are provided only as examples. Additionally, it should be understood that the metrics shown in FIG. 3 were calculated from data included in the example runner's electronic log (see e.g., FIG. 2A). This disclosure contemplates that short-term, medium-term, and/or long-term metrics can be calculated using any tools known in the art including, but not limited to a spreadsheet (e.g., MICROSOFT EXCEL spreadsheets of Microsoft Corp. of Redmond, Wash.), a computer program or application (e.g., MATLAB platform of MathWorks Corp. of Natick, Mass.), or a programming language (e.g., Python) library or toolkit.

A runner profile also includes at least one consistency metric. Consistency metrics include, but are not limited to, a short-term consistency metric, a medium-term consistency metric, and a long-term consistency metric. This disclosure contemplates that a consistency metric represents a number of running days (or number of runs) during the short-term, medium-term, and/or long-term periods. Additionally, this disclosure contemplates that the consistency metrics can be obtained (e.g., received, downloaded, etc.) and/or derived from the electronic runner's log described above. As used herein, a short-term consistency metric is the number of running days or raw number of runs during a training period. For example, if a runner ran every day Monday through Friday during a 7-day training period, then the short-term consistency metric is 5. As used herein, a medium-term consistency metric is the average consistency over a plurality of training periods. For example, if a runner ran 5, 6, and 7 days during each of three consecutive 7-day training periods, respectively, then the medium-term consistency metric is 6. As used herein, a long-term intensity metric is the average consistency over a plurality of training periods. For example, if a runner ran 5, 6, 7, 0, 1, 1, 5, 6, 7, 4, 2, and 4 days during each of twelve consecutive 7-day training periods, respectively, then the long-term consistency metric is 4. The short-, medium-, and long-term consistency metrics represent a runner's training period-to-training period consistency over progressively longer periods of time. Additionally, as described above, consistency can be measured by a number of running days or raw number of runs. This disclosure contemplates that patterns predictive of injury risk are present in the combination of volume, intensity, and consistency metrics found in running-related data.

FIG. 4 is a table illustrating short-term, medium-term, and long-term consistency metrics. For example, the table includes short-term consistency metrics ("Consistency ST"), medium-term consistency metrics ("Consistency MT"), and long-term consistency metrics ("Consistency LT") for an example runner during five consecutive weeks in November and December of 2020. In FIG. 4, the short-term, medium-term, and long-term periods are 1, 3, and 12 weeks, respectively. As described above, these lengths are provided only as examples. Additionally, it should be understood that the metrics shown in FIG. 4 were calculated from data included in the example runner's electronic log (see e.g., FIG. 2A). As described above, this disclosure contemplates that short-term, medium-term, and/or long-term metrics can be calculated using any tools known in the art.

Additionally, a runner profile optionally includes at least one variability metric. Variability metrics include, but are not limited to, a short-term variability metric, a medium-term variability metric, and a long-term variability metric. This disclosure contemplates that a variability metric represents a number of high-intensity running days (or number of high-intensity runs) during the short-term, medium-term, and/or long-term periods. As used herein, a high-intensity run is a run requiring greater than ordinary effort by a runner. For example, a workout and a race are considered high-intensity runs. Additionally, this disclosure contemplates that the variability metrics can be obtained (e.g., received, downloaded, etc.) and/or derived from the electronic runner's log described above. As used herein, a short-term variability metric is the number of high-intensity running days or raw number of high-intensity runs during a training period. For example, if a runner ran with high-intensity (e.g., workout, race, etc.) twice during a 7-day training period, then the short-term variability metric is 2. As used herein, a medium-term variability metric is the average variability over a plurality of training periods. For example, if a runner ran with high intensity (e.g., workout, race, etc.) 2, 1, and 1 days during each of three consecutive 7-day training periods, respectively, then the medium-term variability metric is 1.33. As used herein, a long-term variability metric is the average variability over a plurality of training periods. For example, if a runner ran with high intensity (e.g., workout, race, etc.) 2, 1, 1, 0, 0, 1, 1, 2, 2, 0, 1, and 1 days during each of twelve consecutive 7-day training periods, respectively, then the long-term variability metric is 1. The short-, medium-, and long-term variability metrics capture training period-to-training period high-intensity efforts over progressively longer periods of time. Additionally, as described above, variability can be measured by a number of high-intensity running days or raw number of high-intensity runs. This disclosure contemplates that patterns predictive of injury risk are present in the combination of volume, intensity, consistency, and variability metrics found in running-related data.

FIG. 5 is a table illustrating short-term, medium-term, and long-term variability metrics. For example, the table includes short-term variability metrics ("Variability ST"), medium-term variability metrics ("Variability MT"), and long-term variability metrics ("Variability LT") for an example runner during five consecutive weeks in November and December of 2020. In FIG. 5, the short-term, medium-term, and long-term periods are 1, 3, and 12 weeks, respectively. As described above, these lengths are provided only as examples. Additionally, it should be understood that the metrics shown in FIG. 5 were calculated from data included in the example runner's electronic log (see e.g., FIG. 2A). As described above, this disclosure contemplates that short-term, medium-term, and/or long-term metrics can be calculated using any tools known in the art.

Alternatively or additionally, a runner profile optionally includes at least one long run fraction metric. Long run fraction metrics include, but are not limited to, one or more of a short-term long run fraction metric, a medium-term long run fraction metric, and a long-term long run fraction metric.

This disclosure contemplates that a long run fraction metric represents a long run volume divided by a training period volume. For example, if a runner's longest run during a 7-day training period is 10 miles and the runner's total mileage during the 7-day training period is 50 miles, the long run fraction metric is 0.2. Additionally, this disclosure contemplates that the long run fraction metrics can be obtained (e.g., received, downloaded, etc.) and/or derived from the electronic runner's log described above. As used herein, a short-term long run fraction metric is a long run volume divided by total volume during a training period. For example, the short-term long run fraction metric is 0.2 when a runner's longest run is 10 miles during 7-day training period where total mileage is 50 miles. As used herein, a medium-term long run fraction metric is the average long run fraction metric over a plurality of training periods. For example, if a runner's long run fraction is 0.2, 0.3, and 0.4 during each of three consecutive 7-day training periods, respectively, then the medium-term long run fraction metric is 0.3. As used herein, a long-term long run fraction metric is the average long run fraction metric over a plurality of training periods. For example, if a runner's long run fraction is 0.2, 0.3, 0.4, 0.25, 0.3, 0.25, 0.2, 0.2, 0.4, 0.3, 0.25, and 0.2 during each of twelve consecutive 7-day training periods, respectively, then the long-term long run fraction metric is 0.27. The short-, medium-, and long-term long run fraction metrics capture the training period-to-training period fractional contribution of a runner's longest run to total volume over progressively longer periods of time. This disclosure contemplates that patterns predictive of injury risk are present in the volume, intensity, consistency, variability, long run fraction metrics, or combinations thereof found in running-related data.

FIG. 6 is a table illustrating short-term, medium-term, and long-term long run fraction metrics. For example, the table includes short-term long run fraction metrics ("Long Run Fraction ST"), medium-term long run fraction metrics ("Long Run Fraction MT"), and long-term long run fraction metrics ("Long Run Fraction LT") for an example runner during five consecutive weeks in November and December of 2020. In FIG. 6, the short-term, medium-term, and long-term periods are 1, 3, and 12 weeks, respectively. As described above, these lengths are provided only as examples. Additionally, it should be understood that the metrics shown in FIG. 6 were calculated from data included in the example runner's electronic log (see e.g., FIG. 2A). As described above, this disclosure contemplates that short-term, medium-term, and/or long-term metrics can be calculated using any tools known in the art.

Alternatively or additionally, a runner profile optionally includes at least one dynamic metric. Dynamic metrics include, but are not limited to, a daily dynamic metric, a short-term dynamic metric, a medium-term dynamic metric, and a long-term dynamic metric. Optionally, in some implementations, the dynamic metrics includes a short-term dynamic metric, a medium-term dynamic metric, and a long-term dynamic metric. This disclosure contemplates that a dynamic metric defines an aspect of a runner's motion. Dynamic metrics can be derived from sensor data such as accelerometer or internal sensor data. Example dynamic metrics include, but are not limited to, cadence or stride length. Additionally, this disclosure contemplates that the dynamic metrics can be obtained (e.g., received, downloaded, etc.) and/or derived from the electronic runner's log described above. For example, the table in FIG. 2A includes an example dynamic metric—stride length. As used herein, a daily dynamic metric is a 1-day average dynamic metric such as cadence or stride length. As used herein, a short-term dynamic metric is the average dynamic metric such as cadence or stride length during a training period. As used herein, a medium-term dynamic metric is the average dynamic metric such as cadence or stride length over a plurality of training periods. As used herein, a long-term dynamic metric is the average dynamic metric such as cadence or stride length over a plurality of training periods. The daily, short-, medium-, and long-term dynamic metrics represent average dynamic metrics such as cadence or stride length over progressively longer periods of time. This disclosure contemplates that patterns predictive of injury risk are present in the combination of volume, intensity, consistency, variability, long run fraction, and dynamic metrics found in running-related data.

Alternatively or additionally, a runner profile optionally includes a physiological metric. Physiological metrics include, but are not limited to, a daily physiological metric, a short-term physiological metric, a medium-term physiological metric, and a long-term physiological metric. Optionally, in some implementations, the physiological metrics includes a short-term physiological metric, a medium-term physiological metric, and a long-term physiological metric. Physiological metrics include, but are not limited to, heart rate data, oxygen saturation data, or $VO_2$ max data, for example. Additionally, this disclosure contemplates that the physiological metrics can be obtained (e.g., received, downloaded, etc.) and/or derived from the electronic runner's log described above. For example, the table in FIG. 2A includes an example dynamic metric—heart rate. As used herein, a daily physiological metric is a 1-day average physiological metric such as heart rate during a run. As used herein, a short-term physiological metric is the average physiological metric such as running heart rate during a training period. As used herein, a medium-term physiological metric is the average physiological metric such as running heart rate over a plurality of training periods. As used herein, a long-term physiological metric is the average physiological metric such as running heart rate over a plurality of training periods. The daily, short-, medium-, and long-term physiological metrics represent the average physiological metric over progressively longer periods of time. This disclosure contemplates that patterns predictive of injury risk are present in the combination of volume, intensity, consistency, variability, long run fraction, dynamic, and physiological metrics found in running-related data.

Figure 7:
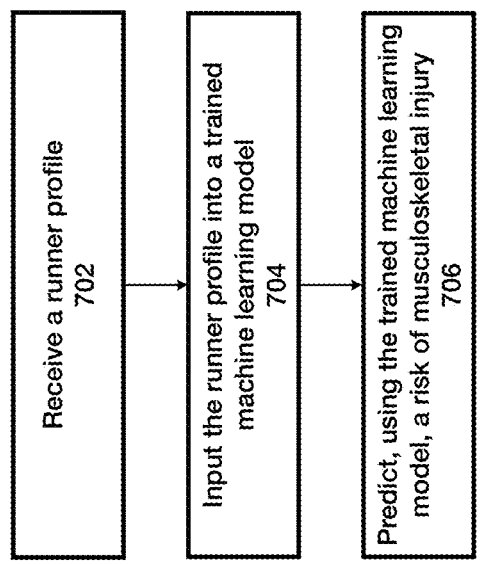
FIG. 7 is a flow diagram illustrating example operations for predicting running-related injury according to an implementation described herein.

Referring now to FIG. 7, an example machine learning-based method for predicting risk of running-related injury is shown. This disclosure contemplates that the method of FIG. 7 can be performed using a computing device, e.g., computing device 1000 shown in FIG. 10. At step 702, a runner profile is received at a computing device. As described herein, the runner profile includes running-related data (see e.g., FIGS. 2A and 2B). Additionally, the runner profile includes at least one volume metric (see e.g., FIG. 3), at least one intensity metric (see e.g., FIG. 3), and at least one consistency metric (see e.g., FIG. 4). Optionally, the runner profile further includes at least one variability metric (see e.g., FIG. 5). Alternatively or additionally, the runner profile optionally further includes at least one long run fraction metric (see e.g., FIG. 6). Alternatively or additionally, the runner profile optionally further includes at least one dynamic metric. Alternatively or additionally, the runner profile optionally further includes at least one physiological metric. As described herein, any one or more of the metrics above can optionally include short-term, medium-term, and/or long-term metrics.

At step 704, the runner profile is input into a trained machine learning model. This disclosure contemplates that the machine learning model is the machine learning model 100 shown in FIG. 1. In other words, the runner profile is the input 110 to the machine learning model 100 of FIG. 1. Additionally, this disclosure contemplates that the machine learning model 100 is trained as described with regard to FIG. 9. Referring again to FIG. 7, the runner profile input into the trained machine learning model may be a vector or tensor (see e.g., FIGS. 19A, 20A, 21A). The "features," which are input into the trained machine learning model, can be extracted from the running-related data (see e.g., FIGS. 2A and 2B). Alternatively or additionally, the features can be various metrics calculated from the running-related data (see e.g., FIGS. 3-6). For example, FIGS. 8A-8D illustrate various features of a runner profile that can be input into the trained machine learning model in some implementations. FIGS. 8A-8D include short-term, medium-term, and long-term metrics for the week of Dec. 13, 2020 for an example runner (see FIGS. 3-6). FIG. 8A includes volume, intensity, and consistency metrics. FIG. 8B includes volume, intensity, consistency, and variability metrics. FIG. 8C includes volume, intensity, consistency, and long run fraction metrics. FIG. 8D includes volume, intensity, consistency, variability, and long run fraction metrics. It should be understood that FIGS. 8A-8D are provided only as example feature combinations and that different metrics or combinations of metrics can be input into the trained machine learning model. Optionally, the features can be scaled before input into the trained machine learning model. Feature scaling may include, but is not limited to, normalizing, standardizing, or converting to z-scores (e.g., number of standard deviations from mean value) the raw data (e.g., data shown in FIGS. 2A-6, 8A-8D, and 11). This disclosure contemplates performing data scaling using tools known in the art including, but not limited to using a spreadsheet (e.g., MICROSOFT EXCEL spreadsheets of Microsoft Corp. of Redmond, Wash.), a computer program or application (e.g., MATLAB platform of MathWorks Corp. of Natick, Mass.), or a programming language (e.g., Python) library or toolkit.

At step 706, a risk of musculoskeletal injury is predicted, using the trained machine learning model, based on the runner profile. In other words, the risk of musculoskeletal injury is the output 120 of the machine learning model 100 of FIG. 1. As described herein, the trained machine learning model is configured to analyze input "features" and predict risk of musculoskeletal injury based on the same. Referring again to FIG. 7, in some implementations, the trained machine learning model outputs a probability of musculoskeletal injury (e.g., a logistic regression). Alternatively, the trained machine learning model classifies the runner profile into a plurality of risk categories (e.g., logistic regression classification). Risk categories can optionally include injury/no injury, low risk/high risk, low risk/medium risk/high risk, etc. classifications. As described herein, the musculoskeletal injury is a running-related injury such as an injury affecting the runner's bones, joints, or soft tissue.

In some implementations, the runner profile input into the model at step 704 includes metrics from the most-recent training period. In other implementations, the runner profile input into the model at step 704 includes metrics calculated for the next (e.g., future) training period. A prospective runner profile can be calculated, for example, based on the runner's training plan (volume, intensity, etc.) for an upcoming training period. FIGS. 19A, 20A, and 21A are tables illustrating example prospective runner profiles that are input into a trained machine learning model. In either implementation, the prediction at step 706 allows the runner to assess, adjust, tailor, etc. his training schedule to minimize likelihood of, or in some cases avoid, suffering a musculoskeletal injury.

Figure 9:
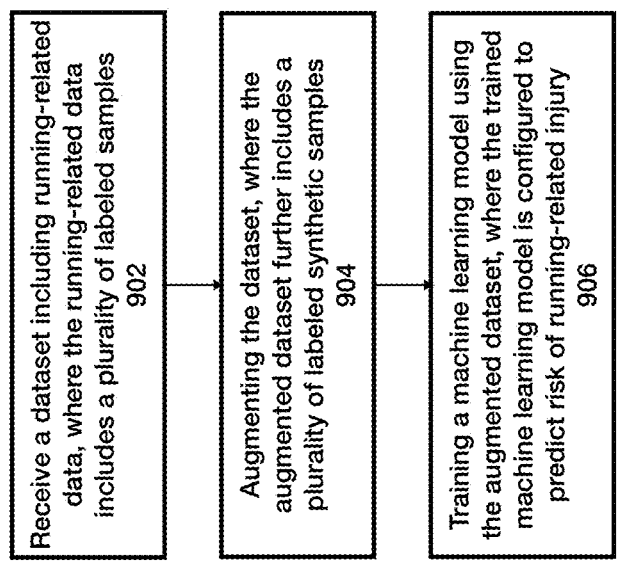
FIG. 9 is a flow diagram illustrating example operations for training a machine learning model according to an implementation described herein.

Referring now to FIG. 9, a flow diagram illustrating example operations for training a machine learning model is shown. This disclosure contemplates that the method of FIG. 9 can be performed using a computing device, e.g., computing device 1000 shown in FIG. 10. At step 902, a dataset including running-related data is received, for example, at the computing device. Optionally, in some implementations, the dataset is maintained (e.g., as a database or structured data) in memory and/or a storage media controlled by and/or accessible to the computing device. This disclosure contemplates that the dataset includes running-related data associated with a single runner (see Examples below and FIGS. 11 and 14). Alternatively, this disclosure contemplates that the dataset includes respective running-related data associated with a plurality of runners. Optionally, in such an implementation, the runners whose running-related data is included in the dataset may be of a similar skill level and/or training level. It should be understood that skill level can be assessed by a runner's actual or target race pace (e.g., 5 kilometer (km), 10 km, 15 km, half marathon, or marathon pace), and training level can be assessed by a runner's current training volume, which may be measured by length (e.g., miles) or duration (e.g., time) and/or intensity, which may be measured by pace (e.g., seconds/mile) or speed (e.g., miles/hour). In other words, when the dataset includes running-related data for multiple runners, it may be limited to including those runners whose volume, intensity, consistency, variability, etc. is similarly situated. This is because injuries suffered by a recreational runner (e.g., relatively low volume and intensity) may not be predictive of injuries suffered by a competitive runner (e.g., relatively high volume and intensity) and vice versa. Aggregating running-related data for a plurality of runners into a dataset increases the size of the dataset, as well as the number of injured state samples.

As described herein, the running-related data includes at least one volume metric (see e.g., FIG. 3), at least one intensity metric (see e.g., FIG. 3), at least one consistency metric (see e.g., FIG. 4), at least one long run fraction metric (see e.g., FIG. 6), at least one variability metric (see e.g., FIG. 5), or combinations thereof. Additionally, the running-related data optionally further includes at least one dynamic metric. Alternatively or additionally, the running-related data optionally further includes at least one physiological metric. It should be understood that one or more of the metrics described above can include short-, medium-, and/or long-term metrics as described herein. Additionally, the dataset is a labeled dataset. In other words, the running-related data includes a plurality of samples tagged with respective running-related injury labels. In the Examples below, the dataset includes running-related data for a single runner (which is grouped by week) including: short-, medium-, and long-term volume metrics; short-, medium-, and long-term intensity metrics; short-, medium-, and long-term consistency metrics; short-, medium-, and long-term variability metrics; short-, medium-, and long-term long run fraction metrics; and injury labels (see e.g., Injury Label columns in FIG. 11 (raw data) and FIG. 14 (scaled data)). A labeled sample includes a plurality of metrics (e.g., all or combinations as described herein) and corresponding injury label found in a row of the dataset (see FIG. 11 and FIG. 14). The metrics in the dataset are the "features" and the labels are the "target." It should be understood that the above dataset is provided only as an example. This disclosure contemplates that the dataset can include more or less features than included in the example above.

At step 904, the dataset is augmented to include synthetic data. It should be understood that running-related injuries, while common (e.g., with an estimated 50% of runners experiencing an injury each year), impact a runner on a relatively infrequent basis. In other words, a given runner typically has significantly more 'healthy' weeks during a given year than 'injury' weeks (i.e., weeks where the runner is not able to run). If this was not the case, then the given runner could not improve performance through training. Improved performance is the result of consistent training. Thus, the dataset including running-related data (whether including data for a single runner or multiple runners) is expected to be unbalanced. This means that significantly fewer target variable observations (i.e., injured state samples) are expected to exist in the dataset than samples from other classes (i.e., non-injured state samples). For example, in the Examples below, the dataset for a single runner before augmentation includes 3 injured state samples and 201 non-injured state samples for the training period between Jan. 1, 2018 and Nov. 28, 2021. Machine learning algorithms are known to struggle with performance (e.g., inaccurate predictions) when trained with unbalanced data due to disparity of classes (e.g., injury state & non-injury state classes in the Examples). To address the problem of disparity of classes in the dataset of running-related data, the dataset is augmented to include synthetic data. Thus, the augmented dataset further includes a plurality of synthetic samples tagged with respective running-related injury labels.

The step of augmenting the dataset includes creating the plurality of synthetic samples from the running-related data. A synthetic sample can be created by adjusting a value of a metric associated with a sample tagged with an injury state label (Injury Label=1). In the Examples below, each of weeks Aug. 31, 2020, Apr. 22, 2019, and Jul. 2, 2018 is a sample tagged with the injury state label (Injury Label=1). Optionally, a synthetic sample is created by adjusting respective values of a plurality of metrics associated with a sample tagged with an injury state label. Additionally, the metric or metrics that are adjusted may optionally be selected randomly and/or the metrics or metrics may be adjusted by a random amount, which increases the value of such metric or metrics. As described herein, the metric whose value is adjusted can be a volume metric, consistency metric, intensity metric, long run fraction metric, variability metric, dynamic metric, or physiological metric.

As described below, synthetic samples can be created in a way that make sense for the specific type of data of interest, i.e., running-related data in the present application. Accordingly, the adjustment can optionally be applied to a short-term metric or metrics when creating synthetic samples. Optionally, the adjustment is applied only to the short-term metric or metrics (i.e., the medium- and long-term metrics are not altered when creating synthetic samples). As noted above, values of short-term metrics for the samples tagged with injury state labels, which are the underrepresented observations in the dataset, are adjusted to create synthetic samples. It should be understood that increasing the values of short-term metrics (e.g., volume, intensity, consistency, long run fraction, etc.) should not change the runner's injury state. In other words, if the runner had increased volume, intensity, consistency, and/or long run fraction during the training period in which an injury occurred, then the runner would have experienced the same result—injury. Running more, farther and/or at higher intensity is not expected to reduce injury risk. On the other hand, if the runner had decreased volume, intensity, consistency, and/or long run fraction during the training period in which an injury occurred, then the runner may not have experienced the same result because such decrease may have allowed the runner to avoid injury. Therefore, an adjustment which increases the value of one or more short-term metrics associated with a sample tagged with an injury state label can be applied to create a synthetic sample. It should be appreciated that, for the intensity metric, increasing the value of speed (e.g., miles per hour) corresponds to decreasing the value of pace (e.g., minutes per mile), where either speed or pace may serve as an intensity metric. The respective values for the medium- and long-term metrics associated with the same sample are not adjusted (i.e., these values remain unchanged). Additionally, such adjustment applied to a short-term metric may be random, e.g., resulting in a random amount of increase in volume, intensity, consistency, long run fraction, etc.

Optionally, knowledge-based limitations may be imposed when creating the plurality of synthetic samples. It should be understood that a given runner has limitations such as physical, mental, fitness, physiological, practical, etc. limitations. In particular, a given runner may not be capable of more than doubling (e.g., 2 times) the value of the short-term volume metric. For example, if a given runner typically averages 40 miles per week (volume metric), then the given runner may not be capable of running 80 or more miles per week. This may be due to physical, mental, fitness, physiological, and/or practical limitations. Thus, it would not make sense to adjust the value of the short-term volume metric more than a threshold amount. Accordingly, a knowledge-based limitation (e.g., maximum 2 times value for volume metric) can be imposed when creating synthetic samples. It should be understood that the maximum 2 times value limitation for the volume metric is provided only as an example. This disclosure contemplates that the maximum value adjustment limitation for volume metric may be less than 2 times value (e.g., 1.1, 1.2, 1.3, 1.4, 1.5, 1.6, 1.7, 1.8, 1.9 times value) or more than 2 times value (e.g., 2.1, 2.2, 2.3, 2.4, 2.5, 2.6, 2.7, 2.8, 2.9 or more times value). Additionally, similar to the volume metric, respective knowledge-based limitations for adjustments of the values of other metrics can be applied. As non-limiting examples, knowledge-based limitations for the values of the long run fraction metric, consistency metric, variability metric, and intensity metric can optionally be maximum of 2 times value, plus 2 (integer) days, plus 2 (integer) high-intensity days, and 20% increase value, respectively. It should be understood that the maximum adjustment limitations to the values for the above metrics are provided only as examples. This disclosure contemplates that the respective maximum adjustment limitations may be less or more than those provided as examples. Additionally, it should be understood that the knowledge-based limitations for the adjustments may be specific to an individual runner (i.e., personalized limitations) or generalized for a plurality of runners. Example knowledge-based limitations for adjustments to values of the volume, long run fraction, consistency, variability, and intensity metrics are shown in the table of FIG. 12.

In the Examples below, a plurality of synthetic samples are created from the three injured state samples (i.e., the rows associated with short-term training periods for weeks of Aug. 31, 2020, Apr. 22, 2019, and Jul. 2, 2018 in FIG. 11) in the dataset. In this example, for each synthetic sample, the value of one of the short-term metrics is randomly selected and then adjusted by a random amount to achieve an increased value for the selected metric. It should be understood that although the value associated with only one short term metric is adjusted when creating each synthetic sample in the Examples that the respective values associated with multiple short-term metrics can be adjusted when creating a synthetic sample. Pseudocode for creating synthetic samples from the Aug. 31, 2020 injured state sample is shown in FIG. 13. It should be understood that similar pseudocode can be used for creating synthetic samples from other injured state samples (e.g., the weeks of Apr. 22, 2019 and Jul. 2, 2018 injured state samples). in FIG. 13, the Aug. 31, 2020 injured state sample resides at row #32 in the data frame ("df3"), and seventy (i.e., i=70) synthetic samples are created from the Aug. 31, 2020 injured state sample using a 'for' loop. It should be understood that the number of synthetic samples created with the pseudocode is provided only as an example. This disclosure contemplates creating any number of synthetic samples needed to create a balanced dataset for model training. As used herein, a balanced dataset includes data samples with an approximately even distribution between classes, e.g., about 50% injured state samples and 50% non-injured state samples. It should be understood that the 50-50 distribution is provided only as an example. This disclosure contemplates that the ratio of injured state samples to non-injured state samples may be in a range between about 40% to about 60%. Additionally, a random non-integer, 'n,' between 0 and 1 is generated to determine which short-term metric's value to adjust for each of the 70 instances of synthetic data created. This ensures that short-term metrics for adjustment are selected randomly and evenly when creating the synthetic samples. Short-term volume, long run fraction, consistency, variability, and intensity (pace) metrics reside in columns #7, 11, 1, 4, and 17, respectively, in the data frame ("df3"). 'If,' 'else if,' and 'else' statements are used to apply a random adjustment to the value of the randomly-selected short-term metric for each instance. Additionally, respective random non-integers between 0 and 1 are generated and used for adjusting values of volume and long run fraction metrics (e.g., by adding 1 to the randomly generated non-integer, which creates a multiplier with value greater than 1 and less than 2), and respective random integers between 0 and 2 are generated and used for adjusting values of consistency and variability metrics (e.g., by adding 1 to the randomly generated integer, which creates an increased value of 1 or 2). The adjustment for value of the intensity (pace) metric is based on randomly generated non-integer, 'n,' described above. The 'if,' 'else if,' and 'else' statements ensure that this adjustment is a 20% or less increase in intensity. It should be understood that the pseudocode shown in FIG. 13 is provided only as an example and that this disclosure contemplates creating synthetic samples using other techniques. Further, the knowledge-based limitations as shown in FIG. 12 are used to control the maximum possible adjusted values for the short-term metrics. This results in random adjusted values for the short-term metrics being in the ranges shown in FIG. 12. It should be understood that the knowledge-based limitations shown in FIG. 12 are examples only.

Optionally, in some implementations, the dataset can be further augmented by creating a plurality of synthetic samples by adjusting a value of a metric associated with a sample tagged with a non-injury state label (Injury Label=0). It should be understood that data augmentation of non-injury state samples can be used to increase the size of the dataset. This can be accomplished in a similar manner as described above. For example, a sample tagged with a non-injury state label can be randomly selected and thereafter a value of a short-term metric associated with such sample can be adjusted. As described above, the short-term metric and/or amount of adjustment can be chosen randomly. In contrast to the above techniques, however, the adjustment used when creating a synthetic sample from a sample tagged with a non-injury state label should decrease the value of a short-term metric. This is for a similar reason as outlined above, for example, decreasing the values of short-term metrics (e.g., volume, intensity, consistency, long run fraction, etc.) should not change the runner's non-injury state. In other words, if the runner had decreased volume, intensity, consistency, and/or long run fraction during the training period, then the runner is likely to experience the same result—no injury. On the other hand, if the runner had increased volume, intensity, consistency, and/or long run fraction during the training period, then the runner may not be guaranteed to experience the same result because such increase increases injury risk. Therefore, an adjustment which decreases the value of one or more short-term metrics associated with a sample tagged with a non-injury state label can be applied to create a synthetic sample. Additionally, while knowledge-based limitations may be applied when creating synthetic data from non-injury state samples, such knowledge-based limitations have less practical value. In particular, when dealing with decreasing values of short-term metrics (e.g., volume, consistency, intensity, long run fraction), there are fewer practical limitations at play. Runners periodically decrease (and sometimes drastically decrease) volume, intensity, etc. of running for various reasons and do so without worrying about increased injury risk or other limitation.

Optionally, in some implementations, running-related data in the dataset is preprocessed. Preprocessing can help avoid garbage in, garbage out issues. For example, preprocessing can include, but is not limited to, data cleaning (e.g., removing unwanted feature(s) and/or 'bad' data), data editing, data reduction, and/or feature scaling. Feature scaling operations include normalization, where feature values are rescaled to a range of [0, 1], or standardization, where feature values are rescaled to have a mean of 0 and standard deviation of 1. Standardization is sometimes referred to as z-score. Data preprocessing is well known in the art and therefore not described further herein. In the Examples below, the raw data in the augmented dataset is cleaned and scaled (FIG. 14) before training the machine learning model and also before inputting a feature tensor into a trained model.

Figure 17:
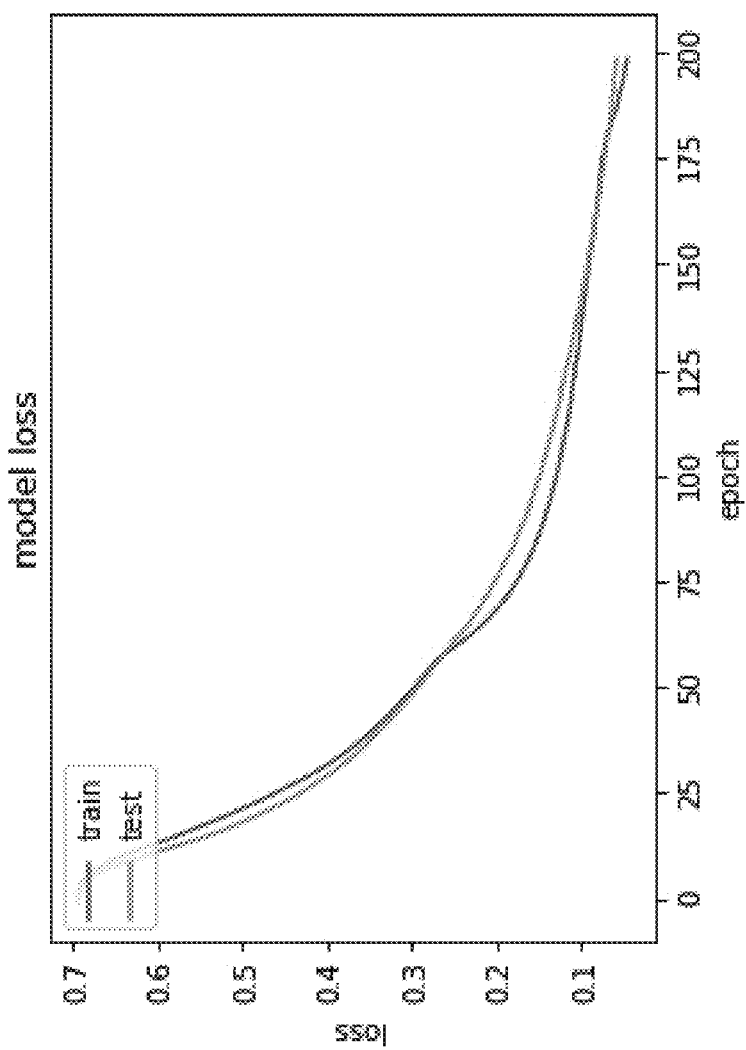
FIG. 17 is a graph illustrating model loss for the ANN of FIG. 16 during training.

Referring again to FIG. 9, a machine learning model is trained using the augmented dataset at step 906. Optionally, the machine learning model is a deep learning model. For example, the deep learning model is optionally a feedforward ANN, which is sometimes referred to as a multilayer perceptron (MLP). It should be understood that ANNs are provided only as an example machine learning model. This disclosure contemplates training other machine learning models including supervised or semi-supervised machine learning models. As described herein, the step of training the machine learning model includes minimizing or maximizing an objective function. Optionally, the objective function is a cost function such as an error between the machine learning model's running-related injury risk prediction and ground truth. Cost functions include, but are not limited to, mean square error, L1 loss (absolute deviations) or L2 loss (least square errors). This disclosure contemplates using any objective function known in the art. FIG. 17 is a graph illustrating model loss for an example machine learning model during model training. The graph illustrates both training loss and testing loss.

As described herein, the trained machine learning model is configured for predicting risk of running-related injury. Thus, the target of training is the runner's injury state—injured or non-injured states. For example, in some implementations, the trained machine learning model is configured to predict risk of running-related injury by providing a classification into one of a plurality of risk categories. In other implementations, the trained machine learning model is configured to predict risk of running-related injury by providing a probability of musculoskeletal injury. Optionally, a target of training in another implementation may be the type of musculoskeletal injury (classification) and/or probability thereof.

Figure 18:
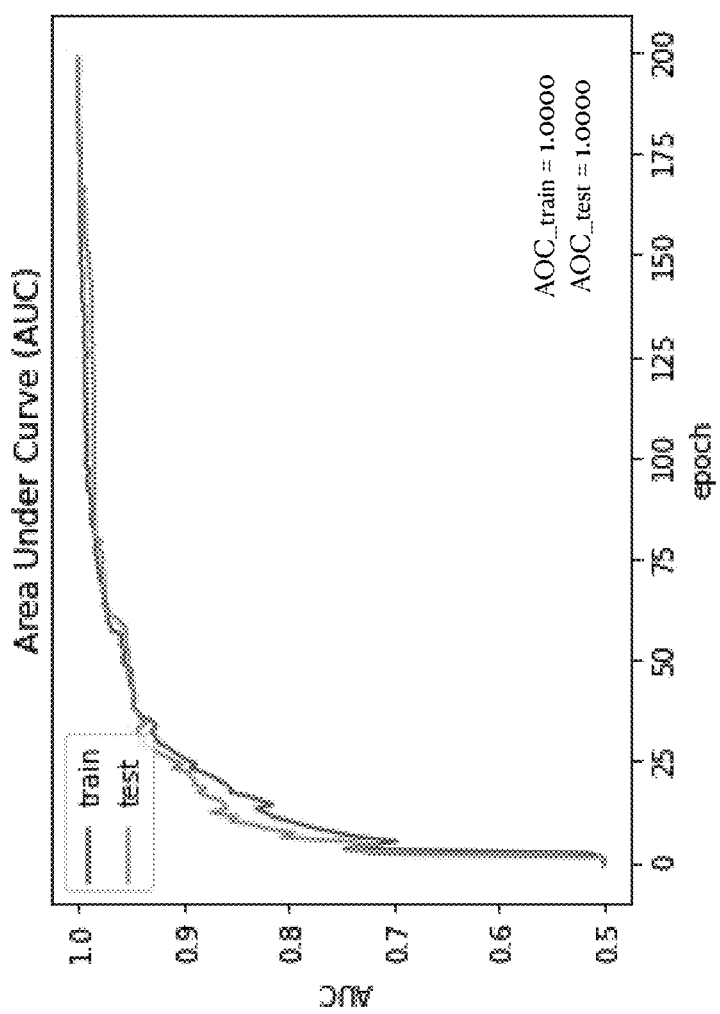
FIG. 18 is a graph illustrating AUC for the ANN of FIG. 16 during training.

Optionally, performance of the machine learning model trained as described with respect to FIG. 9 is evaluated, for example, using an accuracy measure such as an F-score or area under the receiver operator characteristic curve (AUC). F-score is a measure of a model's accuracy that is created from the precision and recall. Precision is a ratio of true positive results to all predicted positive results, which includes true and false positive results. Recall is a ratio of true positive results to all actual positive samples, which includes true positive and false negative results. The receiver operator characteristic (ROC) curve is a plot of true positive rate versus false positive rate over the range of classification thresholds. AUC is the area under ROC curve and provides an aggregate measure of performance across all possible classification thresholds, i.e., a measure of the model's ability to distinguish between classes (e.g., injured state/non-injured state in the Examples). Higher AUC is associated with better performance. A perfect predictor has AUC of 1, while a random predictor has AUC of 0.5. F-score and AUC are known in the art and therefore not described in further detail herein. It should be understood that F-score and AUC are provided only as example model accuracy measures. This disclosure contemplates using other measures to evaluate the trained model's accuracy. FIG. 18 is a graph illustrating AUC for an example machine learning model during model training. The graph illustrates both training AUC and testing AUC.

It should be appreciated that the logical operations described herein with respect to the various figures may be implemented (1) as a sequence of computer implemented acts or program modules (i.e., software) running on a computing device (e.g., the computing device described in FIG. 10), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 10:
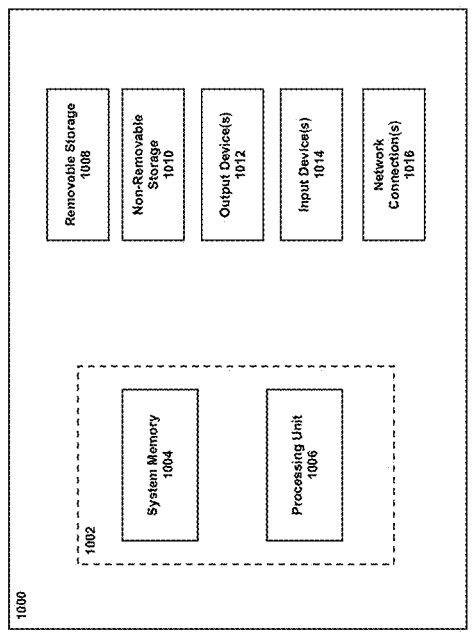
FIG. 10 is an example computing device.

Referring to FIG. 10, an example computing device 1000 upon which the methods described herein may be implemented is illustrated. It should be understood that the example computing device 1000 is only one example of a suitable computing environment upon which the methods described herein may be implemented. Optionally, the computing device 1000 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 1000 typically includes at least one processing unit 1006 and system memory 1004. Depending on the exact configuration and type of computing device, system memory 1004 may be volatile (such as random access memory (RAM)), non-volatile (such as read-only memory (ROM), flash memory, etc.), or some combination of the two. This most basic configuration is illustrated in FIG. 10 by dashed line 1002. The processing unit 1006 may be a standard programmable processor that performs arithmetic and logic operations necessary for operation of the computing device 1000. The computing device 1000 may also include a bus or other communication mechanism for communicating information among various components of the computing device 1000.

Computing device 1000 may have additional features/functionality. For example, computing device 1000 may include additional storage such as removable storage 1008 and non-removable storage 1010 including, but not limited to, magnetic or optical disks or tapes. Computing device 1000 may also contain network connection(s) 1016 that allow the device to communicate with other devices. Computing device 1000 may also have input device(s) 1014 such as a keyboard, mouse, touch screen, etc. Output device(s) 1012 such as a display, speakers, printer, etc. may also be included. The additional devices may be connected to the bus in order to facilitate communication of data among the components of the computing device 1000. All these devices are well known in the art and need not be discussed at length here.

The processing unit 1006 may be configured to execute program code encoded in tangible, computer-readable media. Tangible, computer-readable media refers to any media that is capable of providing data that causes the computing device 1000 (i.e., a machine) to operate in a particular fashion. Various computer-readable media may be utilized to provide instructions to the processing unit 1006 for execution. Example tangible, computer-readable media may include, but is not limited to, volatile media, non-volatile media, removable media and non-removable media implemented in any method or technology for storage of information such as computer readable instructions, data structures, program modules or other data. System memory 1004, removable storage 1008, and non-removable storage 1010 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1006 may execute program code stored in the system memory 1004. For example, the bus may carry data to the system memory 1004, from which the processing unit 1006 receives and executes instructions. The data received by the system memory 1004 may optionally be stored on the removable storage 1008 or the non-removable storage 1010 before or after execution by the processing unit 1006.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, values, etc.), but some errors and deviations should be accounted for.

Example 1

In the examples below, a labeled dataset including running-related data for one individual runner is created. The individual runner is the inventor of the present application. The labeled dataset was collected and used to demonstrate the feasibility of applying machine learning to predict risk of running-related injury. The labeled dataset contains the individual's running-related data downloaded from the GARMIN CONNECT website of Garmin International of Olathe, Kans. in XLS file format. It should be understood that XLS format is only an example and that data may be downloaded in other file formats including, but not limited to, CSV file format. In addition to data downloaded from the GARMIN CONNECT website, each sample (i.e., a week of data residing in a row of FIG. 11) was tagged with a label—0 for non-injury state and 1 for injury state. Thus, the dataset is a labeled dataset. The dataset includes running-related data that is grouped by week for the period between Jan. 1, 2018 and Nov. 28, 2022. Each week (i.e., sample) is tagged with an injury/non-injury label. A labeled sample thus includes a plurality of metrics and corresponding label associated with a given week.

FIG. 11 is an excerpt from a labeled dataset. In FIG. 11 (and others in the Examples), the following metrics appear: short-term consistency (STCon), medium-term consistency (MTCon), long-term consistency (LTCon), short-term variability (STVar), medium-term variability (MTVar), long-term variability (LTVar), short-term volume (STVol), medium-term volume (MTVol), long-term volume (LTVol), maximum volume (Max Vol), short-term long run fraction (STLrf), medium-term long run fraction (MTLrf), long-term long run fraction (LTLrf), short-term duration (STDur), medium-term duration (MTDur), long-term duration (LTDur), short-term intensity (STPac), medium-term intensity (MTPac), long-term intensity (LTPac). These metrics are discussed in detail above. In the Examples, the short-term period is a 7 day period, the medium-term period is a 3 week period, and the long-term period is a 12 week period. Additionally, in the Examples, the volume metric used is measured by distance (miles), but it should be understood that it can alternatively be measured by duration (time). Additionally, in the Examples, the intensity metric used is measured in pace (seconds/mile), but it should be understood that it can alternatively be measured by speed (miles per hour). As described herein, one or more of these metrics serve as features for machine learning. Further, in FIG. 11 (and others in the Examples), the following labels appears: injury state (1) and non-injury state (0). As described herein, the labels serve as the target for machine learning.

The labeled dataset includes 204 samples, which includes 201 samples tagged as non-injury class (Injury Label=0) and 3 samples tagged as injury class (Injury Label=1). The 3 samples tagged as injury class are the weeks of Aug. 31, 2020; Apr. 22, 2019; and Jul. 2, 2018, which represent the weeks of injury occurrence. Each of these samples appears in FIG. 11. The Aug. 31, 2020 injury was to the right calf (possible soleus muscle strain) and resulted in the individual runner taking 4 consecutive days off (i.e., no running) during the following week of Sep. 7, 2020 (see FIG. 2A, Sep. 9-12, 2020). The Apr. 22, 2019 injury was to the right knee (possible patellar tendonitis) and resulted in the individual runner taking a substantial amount of time (i.e., no running) off during the following eight weeks. The Jul. 2, 2018 injury was to the right groin (possible groin strain) and resulted in the individual runner taking 4 consecutive days off (i.e., no running) spanning the weeks of July 2 and 9, 2018.

Example 2

The labeled dataset of Example 1 is unbalanced because samples in the injury class are underrepresented. For example, there are only 3 samples tagged with the injury state label (1), while 201 samples are tagged with the non-injury state label (0). Therefore, the labeled dataset was augmented as described herein. In particular, a plurality of synthetic samples were created based on 3 samples tagged as injury class (i.e., the samples for weeks of Aug. 31, 2020; Apr. 22, 2019; and Jul. 2, 2018), and such synthetic samples were appended to the labeled dataset. 70 synthetic samples were created for each of the samples for weeks of Aug. 31, 2020; Apr. 22, 2019; and Jul. 2, 2018, which resulted in 210 synthetic samples. Thus, the augmented dataset was more balanced having 201 real samples in the non-injury class (Injury Label=0) and 213 actual and synthetic samples in the injury class (Injury Label=1). Each synthetic sample was created by randomly adjusting the value of one short-term metric associated with an injury-labeled sample. Additionally, knowledge-based limitations (see FIG. 12) were applied to the adjusted value of these short-term metrics. Pseudocode used to create a synthetic sample is shown in FIG. 13.

Example 3

After augmenting the dataset, the metrics were scaled. Scaling was accomplished using the PANDAS tool kit in the Python programming language. Both the Python programming language and the PANDAS tool kit, which is a data analysis tool, are well known in the art and therefore not described herein. In particular, the labeled dataset of Example 1 (FIG. 11) and augmented dataset of Example 2 were read into a data frame using the Python programming language. A mean and standard deviation for each metric in the labeled dataset of Example 1 was then calculated. Calculating mean and standard deviation from the labeled dataset of Example 1 (as opposed to the augmented dataset of Example 2) prevented skewing such calculations based on metric values of the synthetic samples, which were created from only 3 real samples in the labeled dataset. Such mean and standard deviation for each metric were then used to scale the metrics in the augmented dataset:

$$\text{Scaled Metric Value} = \frac{\text{Actual Metric Value} - \text{Mean Metric Value}}{\text{Standard Deviation Metric Value}}.$$

The labels (i.e., Injury Label) were left alone and not rescaled. FIG. 14 is an excerpt from an example augmented labeled dataset after data scaling. FIG. 14 shows samples for 5 weeks from Oct. 25, 2021 through Nov. 22, 2021.

Example 4

The scaled, augmented dataset of Example 3 was used to train a machine learning model. Various ANNs were trained using the scaled, augmented dataset. Model training was accomplished using the KERAS tool kit in the Python programming language. Both the Python programming language and the KERAS tool kit, which is a deep learning framework, are well known in the art and therefore not described herein. In particular, the scaled, augmented dataset was read into a data frame using the Python programming language. As described in Examples 2 and 3, the scaled, augmented dataset includes 201 real samples in the non-injury class and 213 real and synthetic samples in the injury class. In the Examples, 80% of the scaled, augmented dataset serves as the training dataset and 20% of the scaled, augmented dataset serves as the testing dataset. Train/test splitting of the scaled, augmented dataset and model training is accomplished using functions in the KERAS tool kit. This includes selecting model architecture and hyperparameters.

As noted above, various ANNs were trained using the scaled, augmented dataset of Example 3 and evaluated for their ability to distinguish between injury/non-injury classes using AUC as the evaluation metric. As described above, AUC provides an aggregate measure of performance across all possible classification thresholds, i.e., a measure of the model's ability to distinguish between the injured state and non-injured state classes. Higher AUC is associated with better performance. FIG. 15 is a table illustrating the AUC analysis for various trained ANNs.

In some implementations, the following 12 metrics serve as model features: short-, medium-, and long-term volume metrics; short-, medium-, and long-term intensity metrics; short-, medium-, and long-term consistency metrics; and short-, medium-, and long-term long run fraction metrics. The model target is the Injury Label. ANNs with different architectures were tested, including ANNs with 1 input layer, 1 hidden layer or 2 hidden layers, and 1 output layer. As an example, an ANN with 1 input layer (12 nodes), 1 hidden layer (4 nodes), and 1 output layer (1 node) is referenced in FIG. 15 as an "ANN with 12/4/1 nodes per layer," and an ANN with 1 input layer (12 nodes), 2 hidden layers (4 nodes, 2 nodes), and 1 output layer (1 node) is referenced in FIG. 15 as an "ANN with 12/4/2/1 nodes per layer." As shown in FIG. 15, the trained ANNs receiving 12 features as input perform very well with AUC equal to 1 or very near equal to 1.

In some implementations, the following 9 metrics serve as model features: short-, medium-, and long-term volume metrics; short-, medium-, and long-term intensity metrics; and short-, medium-, and long-term consistency metrics. The model target is the Injury Label. ANNs with different architectures were tested, including ANNs with 1 input layer, 1 hidden layer or 2 hidden layers, and 1 output layer. As an example, an ANN with 1 input layer (9 nodes), 1 hidden layer (3 nodes), and 1 output layer (1 node) is referenced in FIG. 15 as an "ANN with 9/3/1 nodes per layer," and an ANN with 1 input layer (9 nodes), 2 hidden layers (3 nodes, 2 nodes), and 1 output layer (1 node) is referenced in FIG. 15 as an "ANN with 9/3/2/1 nodes per layer." As shown in FIG. 15, the trained ANNs receiving 9 features as input perform well, but their accuracy is less than that of the trained ANNs receiving 12 features as input. Therefore, including short-, medium-, and long-term long run fraction metrics as model features has advantages that improve ANN performance.

In some implementations, the following 6 metrics serve as model features: short-, medium-, and long-term volume metrics; and short-, medium-, and long-term intensity metrics. The model target is the Injury Label. ANNs with different architectures were tested, including ANNs with 1 input layer, 1 hidden layer or 2 hidden layers, and 1 output layer. As an example, an ANN with 1 input layer (6 nodes), 1 hidden layer (2 nodes), and 1 output layer (1 node) is referenced in FIG. 15 as an "ANN with 6/2/1 nodes per layer," and an ANN with 1 input layer (6 nodes), 2 hidden layers (6 nodes, 3 nodes), and 1 output layer (1 node) is referenced in FIG. 15 as an "ANN with 6/6/3/1 nodes per layer." As shown in FIG. 15, the trained ANNs receiving 6 features as input are less accurate than the trained ANNs receiving 12 or 9 features as input. In fact, the 6/4/2/1 ANN is unable to distinguish between classes with accuracy better than random guessing. Therefore, including short-, medium-, and long-term long run fraction and consistency metrics as model features has advantages that improve performance. Without long run fraction and/or consistency metrics, the trained ANNs do not appear to offer improvement over conventional techniques for predicting running-related injury.

Example 5

Based on the evaluations described in Example 4, an ANN architecture for inference mode was chosen—an ANN with 1 input layer (12 nodes), 2 hidden layers (4 nodes, 2 nodes), and 1 output layer (1 node) as shown in FIG. 16. The trained ANN was saved to a file in a hierarchal data format (HDF) file format. The ANN is configured to distinguish between injured state and non-injured state classes based on the following features: short-, medium-, and long-term volume metrics; short-, medium-, and long-term intensity metrics; short-, medium-, and long-term consistency metrics; and short-, medium-, and long-term long run fraction metrics. This particular ANN architecture was chosen based on its ability to perfectly distinguish between injured state and non-injured state classes (i.e., AUC=1 for both training and testing), as well as its less complex architecture (including only 65 trainable parameters) as compared to other 12-input node ANN architectures with AUC=1. Hyperparameters for the chosen ANN include learning rate=0.001, epochs=200, and batch size=16 as shown in FIG. 16. It should be understood that hyperparameters may be optimized to improve performance, which was not necessary for the chosen ANN. FIG. 17 is a graph illustrating model loss for the ANN of FIG. 16 during training. FIG. 18 is a graph illustrating AUC for the ANN of FIG. 16 during training.

Example 6

The trained ANN of Example 5 and described in FIG. 16 was deployed by the individual runner in inference mode beginning in January 2022. Model deployment was accomplished using the PANDAS, NUMPY, and KERAS tool kits in the Python programming language, which are all well known in the art. In particular, the trained ANN (i.e., HDF file format) and a runner profile (see FIGS. 19A, 20A, 20B in CSV file format) were uploaded using the Python programming language. The runner profile includes the following features: short-, medium-, and long-term volume metrics; short-, medium-, and long-term intensity metrics; short-, medium-, and long-term consistency metrics; and short-, medium-, and long-term long run fraction metrics. The short-term metrics are prospective, i.e., based on the individual runner's training plan for the next week. In other words, the respective values for the short-term volume metric, short-term consistency metric, short-term intensity metric, and short-term long run fraction metric are based on the individual runner's expectations for the next (future) week. Medium- and long-term metrics are calculated accordingly with the prospective data. In the two examples below, the individual runner provides the following expected training information for the upcoming week: volume in miles, long run distance in miles, pace in seconds, and number of training days. Long run fraction is calculated as a ratio of long run distance and volume. Thereafter, the features (12 total), which are scaled as described herein, are input as a tensor into the trained ANN, and the trained ANN outputs a prediction, which classifies the input tensor into one of two classes: the injured state or non-injured state.

In a first example, the trained ANN was used to predict the individual runner's injury state based on the training plan for the upcoming week (future) of Feb. 21, 2022. The individual runner deployed the trained ANN for this purpose on Feb. 20, 2022 using the following prospective data for short-term metrics: 6 training days (STCon), 57 miles total volume (STVol), 0.2632 long run fraction (STLrf) which is based on 15 mile long run, and 468 second/mile (~7:50 min/mi) average pace (STPac). Medium- and long-term metrics were calculated using the prospective and historical data (e.g., resulting in 3 and 12 week averages). This is shown in FIG. 19A. The raw data is in one column, and the scaled data in another in FIG. 19A. The tensor input into the trained ANN is the "scaled data" column in FIG. 19A. The trained ANN output was 0, which corresponds to the non-injured state class, as shown in FIG. 19B. Therefore, the individual runner proceeded according to the training plan for the week of Feb. 21, 2022 and did not experience an injury.

In a second example, the trained ANN was used to predict the individual runner's injury state based on the training plan for the upcoming week (future) of Feb. 28, 2022. In this example, the training plan was adjusted in response to predicted injury. In particular, the individual runner deployed the trained ANN on Feb. 27, 2022 using the following prospective data for short-term metrics: 6 training days (STCon), 60 miles total volume (STVol), 0.3083 long run fraction (STLrf) which is based on 18.5 mile long run, and 479 second/mile (~8:00 min/mi) average pace (STPac). Medium- and long-term metrics were calculated using the prospective and historical data (e.g., resulting in 3 and 12 week averages). This is shown in FIG. 20A. The raw data is in one column, and the scaled data in another in FIG. 20A. The tensor input into the trained ANN is the "scaled data" column in FIG. 20A. The trained ANN output was 1, which corresponds to the injured state class, as shown in FIG. 20B. The individual runner therefore adjusted the training plan using the following prospective data for short-term metrics: 5 training days (STCon), 47.5 miles total volume (STVol), 0.3895 long run fraction (STLrf) which is based on 18.5 mile long run, and 479 second/mile (~8:00 min/mi) average pace (STPac). In other words, the number of training days and total volume were adjusted. Medium- and long-term metrics were calculated using the prospective and historical data (e.g., resulting in 3 and 12 week averages). This is shown in FIG. 21A. The raw data is in one column, and the scaled data in another in FIG. 21A. The tensor input into the trained ANN is the "scaled data" column in FIG. 21A. The trained ANN was then deployed again to predict the individual runner's injury state based on the alternative training plan. The trained ANN output was 0, which corresponds to the non-injured state class, as shown in FIG. 21B. Therefore, the individual runner proceeded according to the alternative training plan (i.e., with fewer training days and less volume) for the week of Feb. 28, 2022 and did not experience an injury.

Accordingly, the individual runner deployed the trained ANN based on his training plans to avoid and/or reduce the risk of musculoskeletal injury. The examples demonstrate the feasibility of using deep learning models to predict running-related injury, as the runner did not experience injury (despite predicted risk thereof for the week of Feb. 28, 2022). As described herein, the ANN was trained to accurately distinguish between samples associated with injured and non-injured states. The datasets described in the Examples, which were used to demonstrate feasibility, are relatively small size. This disclosure contemplates that the techniques described herein can be applied to create a larger data set. Larger datasets can be compiled by collecting running-related data from an individual runner over a longer period of time. Alternatively, larger datasets can be compiled by aggregating running-related data for a plurality of runners. Either case will result in more injured state observations because of the prevalence of injuries. Alternatively or additionally, data augmentation can be used to increase the size of a dataset. As described herein, injury state samples can be altered and appended to the dataset and optionally non-injury state samples can be altered and appended to the dataset. Data augmentation can also be used to balance the dataset.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computer-implemented method for training a machine learning model, comprising:
    collecting a dataset from an electronic runner's log, the dataset comprising running-related data, wherein the running-related data comprises a plurality of samples tagged with respective running-related injury labels;
    creating a plurality of synthetic samples from the running-related data, wherein the plurality of synthetic samples are tagged with respective running-related injury labels;
    creating an augmented dataset comprising the plurality of samples and the plurality of synthetic samples; and
    training a supervised machine learning model using the augmented dataset, wherein training the supervised machine learning model using the augmented dataset is configured to improve performance of the trained supervised machine learning model, wherein the trained supervised machine learning model is configured to predict risk of running-related injury, and wherein the running-related data comprises at least one volume metric, at least one intensity metric, at least one consistency metric, or at least one long run fraction metric.

2. The computer-implemented method of claim 1, wherein a synthetic sample is created by adjusting a value of at least one metric associated with a sample tagged with an injury state label.

3. The computer-implemented method of claim 2, wherein the synthetic sample is created by imposing a knowledge-based limitation on the adjusted value of the at least one metric associated with the sample tagged with the injury state label.

4. The computer-implemented method of claim 1, wherein the running-related data further comprises at least one variability metric.

5. The computer-implemented method of claim 1, wherein the running-related data further comprises at least one dynamic metric.

6. The computer-implemented method of claim 1, wherein the running-related data further comprises at least one physiological metric.

7. The computer-implemented method of claim 1, wherein the running-related data comprises the at least one volume metric, the at least one intensity metric, the at least one consistency metric, and the at least one long run fraction metric.

8. The computer-implemented method of claim 1, wherein the at least one volume metric comprises one or more of a short-term volume metric, a medium-term volume metric, and a long-term volume metric.

9. The computer-implemented method of claim 1, wherein the at least one intensity metric comprises one or more of a short-term intensity metric, a medium-term intensity metric, and a long-term intensity metric.

10. The computer-implemented method of claim 1, wherein the at least one consistency metric comprises one or more of a short-term consistency metric, a medium-term consistency metric, and a long-term consistency metric.

11. The computer-implemented method of claim 1, wherein the at least one long run fraction metric comprises one or more of a short-term long run fraction metric, a medium-term long run fraction metric, and a long-term long run fraction metric.

12. The computer-implemented method of claim 4, wherein the at least one variability metric comprises one or more of a short-term variability metric, a medium-term variability metric, and a long-term variability metric.

13. The computer-implemented method of claim 1, wherein the dataset comprises respective running-related data associated with a plurality of runners.

14. The computer-implemented method of claim 1, wherein the dataset comprises running-related data associated with a single runner.

15. The computer-implemented method of claim 1, wherein the trained supervised machine learning model is configured to predict risk of running-related injury by classifying a runner profile into one of a plurality of risk categories.

16. The computer-implemented method of claim 1, wherein the trained supervised machine learning model is configured to predict risk of running-related injury by providing a probability of musculoskeletal injury for a runner profile.

17. The computer-implemented method of claim 1, wherein training the supervised machine learning model comprises minimizing or maximizing an objective function.

18. The computer-implemented method of claim 17, wherein the objective function is an error between the supervised machine learning model's running-related injury risk prediction and ground truth.

19. The computer-implemented method of claim 1, further comprising evaluating performance of the trained supervised machine learning model using an accuracy measure.

20. The computer-implemented method of claim 1, further comprising preprocessing the dataset or the augmented dataset.

21. The computer-implemented method of claim 20, wherein preprocessing comprises data scaling.

22. The computer-implemented method of claim 1, wherein the supervised machine learning model is a deep learning model.

23. The computer-implemented method of claim 22, wherein the deep learning model is an artificial neural network.

24. A computer-implemented method for predicting risk of running-related injury, comprising:
    training a supervised machine learning model according to claim 1;
    inputting a runner profile into the trained supervised machine learning model; and
    predicting, using the trained supervised machine learning model, a risk of musculoskeletal injury, wherein the risk of musculoskeletal injury is predicted by the trained supervised machine learning model based on the runner profile.

25. The computer-implemented method of claim 24, wherein the runner profile comprises at least one volume metric, at least one intensity metric, at least one consistency metric, at least one long run fraction metric, at least one variability metric, at least one dynamic metric, or at least one physiological metric.

26. The computer-implemented method of claim 24, wherein the runner profile comprises at least one volume metric, at least one intensity metric, at least one consistency metric, and at least one long run fraction metric.

27. The computer-implemented method of claim 24, wherein the risk of musculoskeletal injury is a classification into one of a plurality of risk categories.

28. The computer-implemented method of claim 24, wherein the risk of musculoskeletal injury is a probability of musculoskeletal injury.

29. The computer-implemented method of claim 24, wherein the supervised machine learning model is a deep learning model.

\* \* \* \* \*